(12) United States Patent
Friedman et al.

(10) Patent No.: US 11,191,459 B2
(45) Date of Patent: Dec. 7, 2021

(54) ECG-BASED ANALYTE ASSESSMENTS WITH ADJUSTMENTS FOR VARIANCES IN PATIENT POSTURE

(71) Applicant: Mayo Foundation for Medical Education and Research, Rochester, MN (US)

(72) Inventors: Paul A. Friedman, Rochester, MN (US); Michael J. Ackerman, Rochester, MN (US); Samuel J. Asirvatham, Rochester, MN (US); Itzhak Zachi Attia, Rochester, MN (US); Kevin E. Bennet, Rochester, MN (US); Charles J. Bruce, Ponte Verda, FL (US); John J. Dillon, Rochester, MN (US); Jennifer L. Dugan, Rochester, MN (US); Dorothy J. Ladewig, Mazeppa, MN (US); Virend K. Somers, Rochester, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 148 days.

(21) Appl. No.: 16/332,692

(22) PCT Filed: Sep. 12, 2017

(86) PCT No.: PCT/US2017/051183
§ 371 (c)(1),
(2) Date: Mar. 12, 2019

(87) PCT Pub. No.: WO2018/049402
PCT Pub. Date: Mar. 15, 2018

(65) Prior Publication Data
US 2019/0246966 A1 Aug. 15, 2019

Related U.S. Application Data

(60) Provisional application No. 62/393,634, filed on Sep. 12, 2016.

(51) Int. Cl.
*A61B 5/145* (2006.01)
*A61B 5/11* (2006.01)
(Continued)

(52) U.S. Cl.
CPC ........ *A61B 5/14546* (2013.01); *A61B 5/1116* (2013.01); *A61B 5/316* (2021.01);
(Continued)

(58) Field of Classification Search
CPC .......................... A61B 5/14546; A61B 5/0472
See application file for complete search history.

(56) References Cited

U.S. PATENT DOCUMENTS 7,623,910 B2   11/2009   Courdec et al.
7,991,458 B2    8/2011   Hardahl et al.
(Continued)

FOREIGN PATENT DOCUMENTS

WO   WO-2007137037 A1 * 11/2007 ......... A61N 1/37512
WO   WO 2015/048514        4/2015
(Continued)

OTHER PUBLICATIONS

Ackerman et al., "Epinephrine-induced qt interval prolongation: A gene-specific paradoxical response in congenital long qt syndrome<" Mayo Clin. Proc., 77(5):413-21, May 2002.
(Continued)

*Primary Examiner* — Michael J D Abreu
(74) *Attorney, Agent, or Firm* — Fish & Richardson P.C.

(57) ABSTRACT

Systems, methods, and other techniques for estimating the level of an analyte present in a patient during a time interval
(Continued)

using electrocardiogram (ECG) signals. The estimate can be improved using information about the patient's posture.

23 Claims, 14 Drawing Sheets

(51) Int. Cl.
    A61B 5/316    (2021.01)
    A61B 5/349    (2021.01)
    A61B 5/366    (2021.01)
    A61B 5/00    (2006.01)
    A61B 5/352    (2021.01)

(52) U.S. Cl.
    CPC .............. *A61B 5/349* (2021.01); *A61B 5/366* (2021.01); *A61B 5/352* (2021.01); *A61B 5/6803* (2013.01); *A61B 5/6893* (2013.01); *A61B 5/6898* (2013.01)

(56) References Cited

U.S. PATENT DOCUMENTS

| | | | |
|---|---|---|---|
| 8,126,554 B2 | 2/2012 | Kane et al. | |
| 2005/0222511 A1 | 10/2005 | Hadley et al. | |
| 2007/0208264 A1 | 9/2007 | Hardahl et al. | |
| 2008/0033313 A1 | 2/2008 | Couderc et al. | |
| 2008/0188761 A1* | 8/2008 | Couderc | A61B 5/0452 600/509 |
| 2010/0152801 A1 | 6/2010 | Koh et al. | |
| 2010/0222690 A1 | 9/2010 | Shvilkin et al. | |
| 2012/0179055 A1 | 7/2012 | Tamil et al. | |
| 2014/0057811 A1 | 2/2014 | Athey et al. | |
| 2015/0335288 A1 | 11/2015 | Toth et al. | |
| 2016/0035000 A1 | 2/2016 | Xu | |
| 2016/0135705 A1 | 5/2016 | Liu et al. | |

FOREIGN PATENT DOCUMENTS

| | | |
|---|---|---|
| WO | WO 2016/025297 | 2/2016 |
| WO | WO 2017/091736 | 6/2017 |
| WO | WO 2018/049402 | 3/2018 |

OTHER PUBLICATIONS

Ackerman, "My approach to treatment of the congenital long qt syndromes," Trends Cardiovasc. Med., 25(1):67-9, Jan. 2015.
Antzelevitch and Shimizu, "Cellular mechanisms underlying the long QT syndrome," Curr. Opin. Cardiol., 17(1):43-51, Jan. 2002.
Benhorin et al., "Variable expression of long QT syndrome among gene carriers from families with five different HERG mutations," Ann. Noninvasive Electrocardiol., 7(1):40-6, Jan. 2001.
Chorin et al., "Diagnostic value of t-wave morphology changes during "qt stretching" in patients with long qt syndrome," Heart Rhythm, 12(11):2263-71, Nov. 2015.
Couderc et al., "Impaired T-amplitude adaptation to heart rate characterizes I(Kr) inhibition in the congenital and acquired forms of the long QT syndrome," J. Cardiovasc. Electrophysiol., 18(12):1299-305, Oct. 2007.
Couderc et al., "T-wave morphology abnormalities in benign, potent, and arrhythmogenic I(kr) inhibition," Heart Rhythm, 8(7):1036-43, Jul. 2011.
Dausse et el., "A mutation in herg associated with notched t waves in long qt syndrome," J. Mol. Cell Cardiol., 28(8):1609-15, Aug. 1996.
Einhorn et al., "The frequency of hyperkalemia and its significance in chronic kidney disease," Archives of Internal Medicine, 2009, 169(12):1156-1162.
Gennari et al., "Hypokalemia," New England Journal of Medicine, 1998, 339(7):451-458.
Goldenberg et al., "Corrected qt variability in serial electrocardiograms in long qt syndrome: The importance of the maximum corrected qt for risk stratification," J. Am. Coll. Cardiol., 48(5):1047-52, Sep. 2006.
Gonzalez et al., "A systematic review on the cost-effectiveness of genetic and electrocardiogram testing for long qt syndrome in infants and young adults," Value Health, 18(5):700-8, Jul. 2015.
Goyal et al., "Serum potassium levels and mortality in acute myocardial infarction," JAMA, 2012, 307(2):157-164.
Graff et al., "Identifying drug-induced repolarization abnormalities from distinct ECG patterns in congenital long QT syndrome: a study of sotalol effects on T-wave morphology," Drug Saf., 32(7):599-611, Jul. 2009.
Gumz et al., "An Integrated View of Potassium Homeostasis," New England Journal of Medicine, 2015, 3 73(1):60-72.
Gupta et al., "T(p-e)/QT ratio as an index of arrhythmogenesis," J. Electrocardiol., 41(6):567-74, Nov. 2008.
Haarmark et al., "The prognostic value of the Tpeak-Tend interval in patients undergoing primary percutaneous coronary intervention for ST-segment elevation myocardial infarction," J. Electrocardiol., 42(6):555-60, Nov. 2009.
Haugaa et al., "Institution-wide QT alert system identifies patients with a high risk of mortality," Mayo Clin. Proc., 88(4):315-25, Apr. 2013.
Hondeghem, "Thorough QT/QTc not so thorough: removes torsadogenic predictors from the T-wave, incriminates safe drugs, and misses profibrillatory drugs," J. Cardiovasc. Electrophysiol., 17(3):337-40, Mar. 2006.
International Report on Patentability in Application No. PCT/US20117/051183, dated Nov. 13, 2017, 5 pages.
International Search Report and Written Opinion in Application No. PCT/US2017/051183, dated Nov. 13, 2017, 6 pages.
Jain et al., "Predictors of hyperkalemia and death in patients with cardiac and renal disease," The American journal of cardiology, 2012, 109:1510-1513.
Juurlink et al., "Rates of hyperkalemia after publication of the Randomized Aldactone Evaluation Study," New England Journal of Medicine, 2004, 351:543-551.
Kannankeril et al., "Drug-induced long QT syndrome," Pharmacol. Rev., 62(4):760-8, Dec. 2010.
Kanters et al., "T wave morphology analysis distinguishes between kv1qt1 and herg mutations in long qt syndrome," Heart Rhythm, 1(3):285-92, Sep. 2004.
Kapa et al., "Genetic testing for long-qt syndrome: Distinguishing pathogenic mutations from benign variants," Circulation, 120(18):1752-60, Oct. 2009.
Khositseth et al., "Epinephrine-induced t-wave notching in congenital long qt syndrome," Heart Rhythm, 2(2):141-6, Feb. 2005.
Kovesdy, "Management of hyperkalaemia in chronic kidney disease," Nat Rev Nephrol, 2014, 10:653-662.
Lehmann et al., "T wave "humps" as a potential electrocardiographic marker of the long QT syndrome," J. Am. Coll. Cardiol., 24(3):746-54, Sep. 1994.
Lehtonen et al., "Further evidence of inherited long QT syndrome gene mutations in antiarrhythmic drug-associated torsades de pointes," Heart Rhythm 4(5):603-7, May 2007.
Letsas et al., "Tpeak-Tend interval and Tpeak-Tend/QT ratio as markers of ventricular tachycardia inducibility in subjects with Brugada ECG phenotype," Europace, 12(2):271-4, Feb. 2010.
Malfatto et al., "Quantitative analysis of t wave abnormalities and their prognostic implications in the idiopathic long qt syndrome," J. Am. Coll. Cardiol., 23(2):296-301, Feb. 1994.
Matsuda, "Magnesium gating of the inwardly rectifying K+ channel," Annu. Rev. Physiol., 53(1):289-98, Mar. 1991.
Moss et al., "ECG T-wave patterns in genetically distinct forms of the hereditary long QT syndrome," Circulation, 92(10):2929-34, Nov. 1995.
Numaguchi et al., "A sensitive mechanism for cation modulation of potassium current," Nat. Neurosci., 3(5):429-30, May 2000.
Pavriet et al., "T wave slopes: a novel method for assessment of repolarization dispersion from surface ECGS with prolonged AT as compaered to normal ECGs," J. Am. Coll. Cardiol., 63(Suppl. 12):A1638, Apr. 2014.

(56) References Cited

OTHER PUBLICATIONS

Perez et al.,"Cost-effectiveness of genetic testing in family members of patients with long-qt syndrome," Circ. Cardiovasc. Qual. Outcomes, 4(1):76-84, Jan. 2011.
Priori et al., "HRS/EHRA/APHRS expert consensus statement on the diagnosis and management of patients with inherited primary arrhythmia syndromes," Heart Rhythm, 10(12):1932-63, Dec. 2013.
Roden, "Drug-induced prolongation of the QT interval," N. Eng. J. Med., 350(10):1013-22, Mar. 2004.
Roger et al., "Heart Disease and Stroke Statistics—2012 Update: A Report From the American Heart Association," Circulation, 2012, 125:e2-e220.
Rushing et al., "A leave-one-out cross-validation SAS macro for the identification of markers associated with survival," Comput. Biol. Med., 57:123-9, Feb. 2015.
Sara et al., "Electrocardiographic predictors of coronary microvascular dysfunction in patients with non-obstructive coronary artery disease: Utility of a novel T wave analysis program," 203:601-6, Nov. 2015.
Schwartz and Crotti., "Qtc behavior during exercise and genetic testing for the long-qt syndrome," Circulation, 124(20):2181-4, Nov. 2011.
Schwartz et al., "Genotype-phenotype correlation in the long-QT syndrome: gene-specific triggers for life-threatening arrhythmias," Circulation, 03(1):89-95, Jan. 2001.
Schwartz et al., "Prevalence of the congenital long-QT syndrome." Circulation, 120(18):1761-7, Nov. 2009.
Shimizu et al., "T-peak to T-end interval may be a better predictor of high-risk patients with hypertrophic cardiomyopathy associated with a cardiac troponin I mutation than QT dispersion," Clin. Cardiol., 25(7):335-9, Jul. 2002.
Sugrue et al., "Electrocardiographic predictors of torsadogenic risk during dofetilide or sotalol initiation: utility of a novel T wave analysis program," Cardiovas. Drugs Ther., 29(5):433-41, Oct. 2015.
Sugrue et al., "Identification of Concealed and Manifest Long QT Syndrome Using a Novel T Wave Analysis Program," Circ. Arrhythm. Electrophysiol., 9(7):e003830, Jul. 2016.
Sugrue et al., "Identification of Genotype-specific Electrocardiogram Patterns in Long QT Syndrome Using a Novel, Automated T Wave Analysis Program," Circulation, 132(Suppl. 3):A17604, Nov. 2015.
Swan et al., "Sinus node function and ventricular repolarization during exercise stress test in long qt syndrome patients with kv1qt1 and herg potassium channel defects," J. Am. Coll. Cardiol., 34(3):823-9, Sep. 1999.
Sy et al., "Derivation and validation of a simple exercise-based algorithm for prediction of genetic testing in relatives of 1qts probands," Circulation, 124(20):2187-94, Oct. 2011.
Takenaka et al., "Exercise stress test amplifies genotype-phenotype correlation in the 1qt1 and 1qt2 forms of the long-qt syndrome," Circulation, 107(6):838-44, Feb. 2003.
Tanabe et al., "Sympathetic stimulation produces a greater increase in both transmural and spatial dispersion of repolarization in 1qt1 than 1qt2 forms of congenital long qt syndrome," J. Am. Coll. Cardiol., 37(3):911-9, Mar. 2001.

Thomsen et al., "Beat-to-Beat variability of repolarization determines proarrhythmic outcome in dogs susceptible to drug-induced torsades de pointes," J. Am. Coll. Cardiol., 48(6):1268-76, Sep. 2006.
Topilski et al., "The morphology of the QT interval predicts torsade de pointes during acquired bradyarrhythmias," J. Am. Coll. Cardiol., 49(3):320-8, Jan. 2007.
Vandenberg, "Inward rectification of a potassium channel in cardiac ventricular cells depends on internal magnesium ions," Proc. Natl. Acad. Sci. USA, 84(8):2560-4, Apr. 1987.
Veerman et al., "Slow delayed rectifier potassium current blockade contributes importantly to drug-induced long QT syndrome," Circ. Arrhythm. Electrophysiol., 6(5):1002-9, Oct. 2013.
Viitasalo et al., "Differentiation between 1qt1 and 1qt2 patients and unaffected subjects using 24-hour electrocardiographic recordings," Am. J. Cardiol., 89(6):679-85, Mar. 2002.
Vincent et al., "The spectrum of symptoms and qt intervals in carriers of the gene for the long-qt syndrome," N. Engl. J. Med., 327(12):846-52, Sep. 1992.
Viskin et al., "Provocation of sudden heart rate oscillation with adenosine exposes abnormal qt responses in patients with long qt syndrome: A bedside test for diagnosing long qt syndrome," Eur. Heart J., 27(4):469-75, Feb. 2006.
Viskin et al., "The response of the qt interval to the brief tachycardia provoked by standing: A bedside test for diagnosing long qt syndrome," J. Am. Coll. Cardiol., 55(18):1955-61, May 2010.
Vyas and Ackerman, "Epinephrine qt stress testing in congenital long qt syndrome," J. Electrocardiol., 39(4):S107-13, Oct. 2006.
Weiner et al., "Hyperkalemia: a potential silent killer," Journal—American Society of Nephrology, 1998, 9:1535-1543.
Wild et al., "Global prevalence of diabetes estimates for the year 2000 and projections for 2030," Diabetes care, 2004, 27(10):1047-1053.
Wilde and Bezzina, "Genetics of cardiac arrhythmias," Heart, 91(10):1352-8, Sep. 2005.
Wong et al., "Utility of treadmill testing in identification and genotype prediction in long-qt syndrome," Circ. Arrhythm. Electrophysiol., 3(2):120-125, Apr. 2010.
Yan and Antzelevitch, "Cellular basis for the normal T wave and the electrocardiographic manifestations of the long-QT syndrome," Circulation, 98(18):1928-36, Nov. 1998.
Yang and Roden, "Extracellular potassium modulation of drug block of IKr, Implications for torsade de pointes and reverse use-dependence," Circulation, 93(3):407-11, Feb. 1996.
Yang et al., "Allelic variants in long-QT disease genes in patients with drug-associated torsades de pointes," Circulation, 105(16):1943-8, Apr. 2002.
Yang et al.. "Rapid inactivation determines the rectification and [K+]o dependence of the rapid component of the delayed rectifier K+ current in cardiac cells," Circ. Res., 80(6):782-9, Jun. 1997.
Yap and Camm,"Drug induced QT prolongation and torsades de pointes," Heart, 89(11):1363-72, Nov. 2003.
Zareba, "Challenges of diagnosing long qt syndrome in patients with nondiagnostic resting qtc," J. Am. Coll. Cardiol., 55(18):1962-4, May 2010.
Zhang et al., "Spectrum of ST-T-wave patterns and repolarization parameters in congenital long-QT syndrome: ECG findings identify genotypes," Circulation, 102(23):2849-55, Dec. 2000.

\* cited by examiner

600 ↴

```
┌─────────────────────────────────────────────────────────┐
│ Obtain baseline QRS model that characterizes baseline QRS features │
│ of a patient's ECG vector from one or more lead pairs coupled to the │
│ patient when the patient is in a baseline position    602 │
└─────────────────────────────────────────────────────────┘
                            ↓
┌─────────────────────────────────────────────────────────┐
│ Monitor ECG data sensed by the one or more lead pairs, including │
│ comparing respective QRS features for multiple beats represented in │
│ the ECG data to the baseline QRS features             604 │
└─────────────────────────────────────────────────────────┘
                            ↓
┌─────────────────────────────────────────────────────────┐
│ Select a particular beat, among the multiple beats, having QRS │
│ features that closely match the baseline QRS features │
│                                                       606 │
└─────────────────────────────────────────────────────────┘
                            ↓
┌─────────────────────────────────────────────────────────┐
│ Determine estimated analyte level based on T-wave features derived │
│ from ECG vector for the selected beat and patient's ECG-analyte │
│ model                                                 608 │
└─────────────────────────────────────────────────────────┘
                            ↓
┌─────────────────────────────────────────────────────────┐
│ Output indication of estimated analyte level          │
│                                                       610 │
└─────────────────────────────────────────────────────────┘
```

FIG. 6

ECG-BASED ANALYTE ASSESSMENTS WITH ADJUSTMENTS FOR VARIANCES IN PATIENT POSTURE

CROSS-REFERENCE TO RELATED APPLICATIONS

This application is a National Stage application under 35 U.S.C. § 371 of International Application No. PCT/US2017/051183, having an International Filing Date of Sep. 12, 2017, which claims priority to U.S. Application Ser. No. 62/393,634, filed on Sep. 12, 2016. The disclosures of the prior applications are considered part of the disclosure of this application, and are incorporated in their entirety into this application.

STATEMENT OF GOVERNMENT SUPPORT

This invention was made with government support under AG047716 and EB017649 awarded by the National Institute of Health. The government has certain rights in the invention.

TECHNICAL FIELD

This document generally describes computer-based technology for analyzing physiological electrical data (e.g., electrocardiogram data).

BACKGROUND

Electrocardiograms are commonly used to assess the electrical activity of a patient's heart. The tracing of an electrocardiogram can show a patient's cardiac rhythm and may include various segments that represent different portions of the rhythm for each beat. For example, different segments may correspond to each of a P-wave, a QRS-complex, and a T-wave. Because a number of physiological conditions of a patient may impact the electrical activity of a patient's heart, studies have linked characteristics of a patient's electrocardiogram to various conditions. Some studies have shown a link between characteristics of a patient's electrocardiogram and levels of potassium in the patient's system.

Blood potassium levels are tightly homeostatically regulated, and critical for normal physiologic cellular function. See Einhorn L M, Zhan M, Walker L D, Moen M F, Seliger S L, Weir M R, Fink J C: The frequency of hyperkalemia and its significance in chronic kidney disease. Archives of Internal Medicine 169, 1156-1162 (2009); Goyal A, Spertus J A, Gosch K: Serum potassium levels and mortality in acute myocardial infarction. JAMA 307, 157-164, doi:10.1001/jama.2011.1967 (2012). Fluctuations in potassium values are found in many disease states and can expose patients to life threatening arrhythmias. See Gennari, F. J. Hypokalemia. New England Journal of Medicine 339, 451-458, doi:doi:10.1056/NEJM199808133390707 (1998); Weiner, I. D. & Wingo, C. S. Hyperkalemia: a potential silent killer. JOURNAL-AMERICAN SOCIETY OF NEPHROLOGY 9, 1535-1543 (1998); Kovesdy, C. P. Management of hyperkalaemia in chronic kidney disease. Nat Rev Nephrol 10, 653-662, doi:10.1038/nrneph.2014.168 (2014). There is compelling evidence that in patients with renal or cardiac disease, even modest potassium changes may lead to morbidity, hospitalization, and death. See Jain N, Kotla S, Little B B, Weideman R A, Brilakis E S, Reilly R F, Banerjee S: Predictors of hyperkalemia and death in patients with cardiac and renal disease. The American journal of cardiology 109, 1510-1513 (2012). Moreover, evidence-based therapies used to treat these conditions, including adrenergic blockade, potassium sparing diuretics and renin-angiotensin antagonism, can result in hyper or hypokalemia. After the potassium-sparing diuretic spironolactone was shown to lower heart failure mortality in a randomized prospective trial, hospitalization for hyperkalemia tripled, and mortality doubled. See Juurlink D N, Mamdani M M, Lee D S, Kopp A, Austin P C, Laupacis A, Redelmeier D A: Rates of hyperkalemia after publication of the Randomized Aldactone Evaluation Study. New England Journal of Medicine 351, 543-551 (2004).

As the prevalence of these diseases and their risk factors (hypertension and diabetes) rise, and as the population continues to age, increasing numbers of patients will be at risk of hyperkalemia and hypokalemia. See Wild, S., Roglic, G., Green, A., Sicree, R. & King, H. Global prevalence of diabetes estimates for the year 2000 and projections for 2030. Diabetes care 27, 1047-1053 (2004); Roger V L, Go A S, Lloyd-Jones D M, Benjamin E J, Berry J D, Borden W B, Bravata D M, Dai S, Ford E S, Fox C S, Fullerton H J, Gillespie C, Hailpern S M, Heit J A, Howard V J, Kissela B M, Kittner S J, Lackland D T, Lichtman J H, Lisabeth L D, Makuc D M, Marcus G M, Marelli A, Matchar D B, Moy C S, Mozaffarian D, Mussolino M E, Nichol G, Paynter N P, Soliman E Z, Sorlie P D, Sotoodehnia N, Turan T N, Virani S S, Wong N D, Woo D, Turner M B; American Heart Association Statistics Committee and Stroke Statistics Subcommittee. Heart Disease and Stroke Statistics-2012 Update: A Report From the American Heart Association. Circulation 125, e2-e220, doi:10.1161/CIR.0b013e31823ac046 (2012).

Potassium levels outside the normal range are concerning, as they are usually clinically silent, occurring without warning to the patient or provider in the absence of blood tests. See Gumz, M. L., Rabinowitz, L. & Wingo, C. S. An Integrated View of Potassium Homeostasis. New England Journal of Medicine 373, 60-72, doi:doi:10.1056/NEJMra1313341 (2015).

SUMMARY

This specification discloses computer-based systems, methods, devices, and other techniques for estimating levels of an analyte (e.g., potassium, magnesium, phosphorous) in a patient based on features of the patient's electrocardiogram (ECG). Further, because the ECG for a patient can change as he or she moves and assumes different positions (e.g., changes pose or posture) during the course of ECG monitoring, the techniques described herein provide a system that can compensate for changes in the ECG resulting from patient movement so that a reliable estimation of the level of an analyte can still be determined while the patient is ambulatory or otherwise assumes different positions.

Some implementations of the subject matter described herein include a computer-implemented method. The method can include receiving, by a computing system, electrocardiogram (ECG) data that characterizes physiological electrical activity of a patient during a first time interval, the ECG data corresponding to signals sensed by electrodes for a plurality of leads physically coupled to the patient. The computing system determines whether a position of the patient during the first time interval matches a pre-defined baseline position of the patient. In response to determining that the position of the patient during the first time interval does not match the pre-defined baseline position, the computing system selects a particular pair of leads, among the plurality of leads, based on a level of similarity between first waveform features of an ECG vector for the particular pair of leads and a pre-defined set of waveform features. The computing system generates, based on at least one of (i) second waveform features of the ECG vector for the particular pair of leads or (ii) waveform features of a derived ECG vector computed using the ECG vector for the particular pair of leads, an estimation of a level of an analyte present in the patient during the first time interval. An indication is provided of the estimated level of the analyte that is present in the patient during the first time interval.

Some implementations of the subject matter described herein include a computer-implemented method. The method includes obtaining, by a computing system and for each electrode of a set of three or more electrodes physically coupled to a patient, data that represents an electrocardiogram (ECG) signal sensed by the electrode over a first time interval; determining, by the computing system, a plurality of ECG vectors, wherein each ECG vector of the plurality of ECG vectors corresponds to a unique pair of electrodes from the set of electrodes and represents a difference between the respective ECG signals sensed by the unique pair of electrodes; selecting, by the computing system, a preferred ECG vector from among the plurality of ECG vectors; and generating, based on the selection, a visual or audible notification of the unique pair of electrodes that corresponds to the preferred ECG vector.

These and other implementations can optionally include one or more of the following features.

The computing system may further determine a respective set of one or more waveform features that characterize one or more beats from each of the plurality of ECG vectors. The preferred ECG vector can be selected based on the respective set of waveform features for the preferred ECG vector.

Generating the visual or audible notification of the unique pair of electrodes that corresponds to the preferred ECG vector can include illuminating particular visual indicators on a device that includes the set of electrodes that are physically coupled to the patient. The particular visual indicators can be associated with the unique pair of electrodes that correspond to the preferred ECG vector.

Generating the visual or audible notification can include displaying, on a display screen of a computing device, a visual indicator of the unique pair of electrodes that corresponds to the preferred ECG vector.

The computing device can be a smartphone or tablet computer.

The method can further include removing the set of electrodes from the patient and physically coupling a second set of electrodes to the patient such that a first pair of electrodes in the second set of electrodes is positioned in a same location and orientation as the unique pair of electrodes that corresponds to the preferred ECG vector.

Some implementations of the subject matter described herein includes a computer-implemented method. The method includes obtaining, for each electrode of a set of three or more electrodes physically coupled to a patient, data that represents an electrocardiogram (ECG) signal sensed by the electrode over a first time interval; determining a plurality of ECG vectors, wherein each ECG vector of the plurality of ECG vectors corresponds to a unique pair of electrodes from the set of electrodes and represents a difference between the respective ECG signals sensed by the unique pair of electrodes; selecting a preferred ECG vector from among the plurality of ECG vectors; and generating, based on the selection, a visual or audible notification of the unique pair of electrodes that corresponds to the preferred ECG vector.

Some implementations of the subject matter described herein includes a computer-implemented method. The method includes receiving, by a computing system, electrocardiogram (ECG) data that characterizes physiological electrical activity of a patient during a first time interval, the ECG data corresponding to signals sensed by electrodes for a plurality of leads physically coupled to the patient; determining, by the computing system, whether a position of the patient during the first time interval matches a pre-defined baseline position of the patient; in response to determining that the position of the patient during the first time interval does not match the pre-defined baseline position, selecting a particular pair of leads, among the plurality of leads, based on a level of similarity between first waveform features of an ECG vector for the particular pair of leads and a pre-defined set of waveform features; generating, by the computing system based on at least one of (i) second waveform features of the ECG vector for the particular pair of leads or (ii) waveform features of a derived ECG vector computed using the ECG vector for the particular pair of leads, an estimation of a level of an analyte present in the patient during the first time interval; and providing an indication of the estimated level of the analyte that is present in the patient during the first time interval.

Additional aspects include one or more computer-readable media having instructions stored thereon that, when executed by one or more data processing apparatus (e.g., processors), cause the data processing apparatus to perform operations for any of the methods disclosed herein. Additionally, computing systems may include the computer-readable media having the stored instructions and the one or more data-processing apparatus.

This application incorporates by reference in its entirety the contents of PCT Publication No. WO2015/048514.

DESCRIPTION OF DRAWINGS

FIG. 6 depicts a flowchart of an example process for estimating a level of an analyte in a patient using waveform features from a selected ECG vector.

Like references and indicators among the drawings indicate like elements.

DETAILED DESCRIPTION

This specification discloses computer-based systems, methods, devices, and other techniques for analyzing and determining characteristics of electrocardiogram ("ECG") signals. Healthcare professionals have long administered ECGs to patients to evaluate patients' heartbeats, sinus rhythms, and the like. Visual inspection of ECGs, whether recorded by analog or digital means, has facilitated the identification of various diseases and other patient conditions, such as dysrhythmias, heart murmurs, and possible myocardial infarction. More recently, research has shown that various characteristics (e.g., features) of a patient's ECG sometimes provide strong indicators of a range of additional patient conditions that were not conventionally evaluated using ECG data. By way of example, it has been shown that concentrations of analytes (e.g., potassium) in a patient's bloodstream can be estimated by analysis of the patient's ECG. Electrocardiograms can thus provide an effective, non-invasive solution for identification and evaluation of patient conditions that have been correlated with one or more characteristics of an ECG signal.

In the context of this document, ECG data generally refers to a recording of the electrical activity of a mammal's cardiovascular activity (e.g. heartbeat of a patient or other human). The ECG data may be recorded from a traditional surface ECG electrode, custom body surface electrodes that may vary in size, shape, and/or inter-electrode distance, for example, and/or from intracoporeal electrodes, whether they be subcutaneous, intracardiac, or within other tissues or natural cavities. ECGs from which such data is obtained may be spontaneous, or in response to a stimulus or provocation, and may be recorded from contact or non-contact electrodes. In some examples, electrogram data may be obtained from one or more of a standard 12 lead ECG, a wearable patch with one or more channels, and wearable elements including shirts, watches, bands and bracelets with conductive elements capable of recording physiologic signals. ECG data may be obtained in some examples from implanted devices such as loop recorders, pacemakers, and/or defibrillators.

While the term "computer-based" is applied, it is recognized that this may refer to any suitable form of computer processing, including mobile-based processing. For example, the techniques disclosed herein may be implemented at least in part by a mobile computing device such as a smartphone, tablet, or notebook computer that communicates with a system of wearable or hand-held electrodes. These techniques permit data compression and distribution of processing among various aspects of such a system, to enable near real-time, frequent, assessment of ECG features in ambulatory/outpatient individuals. Additionally, this paper broadly uses the term "patient" to generally include any person from whom ECG data is obtained, regardless of their clinical status for example.

Figure 1:
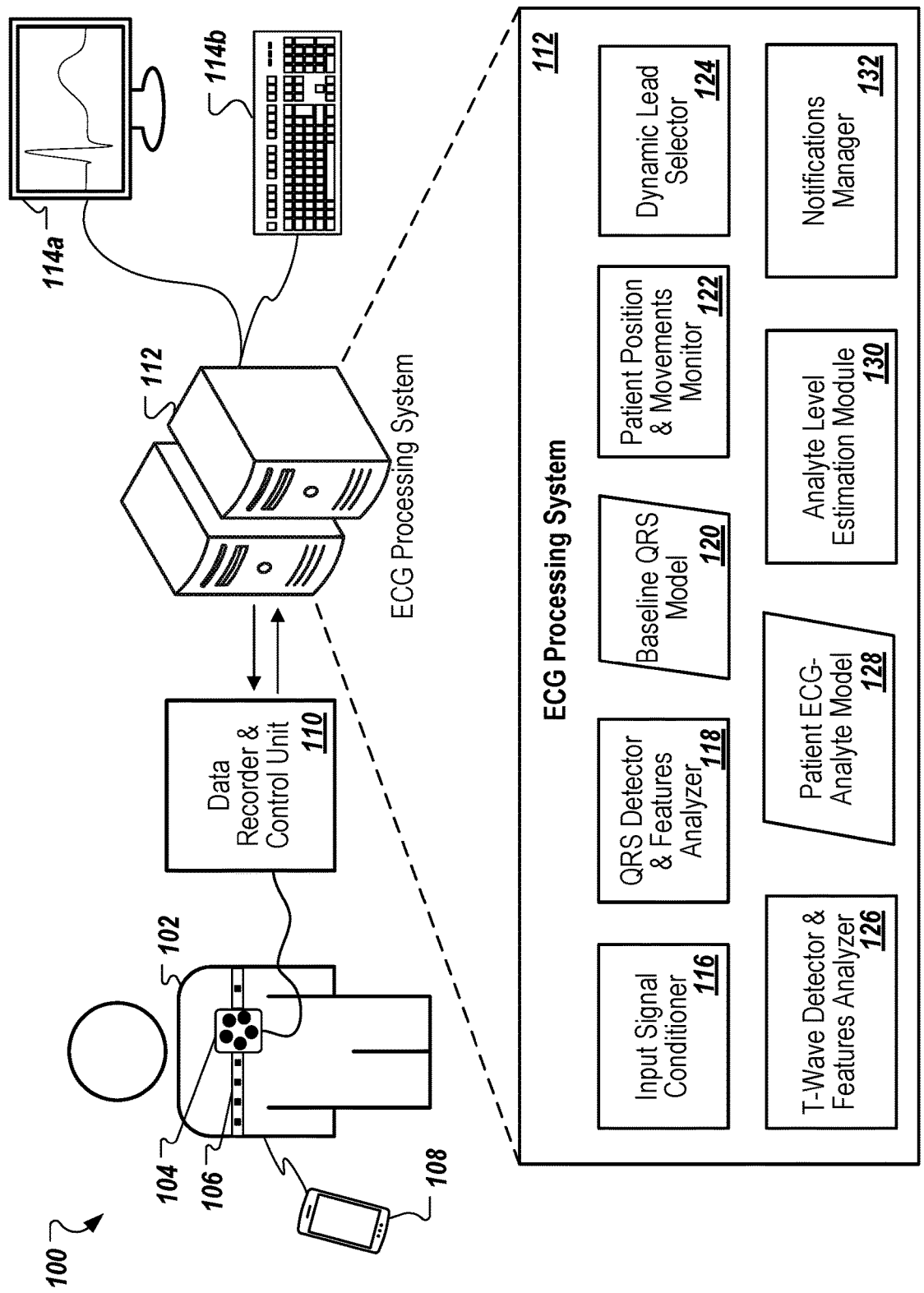
FIG. 1 is a conceptual diagram of an example system for obtaining and processing electrocardiogram (ECG) data. The system includes an ECG processing computing system configured to determine estimated levels of analytes present in a patient based on ECG data, and to account for variances in a patient's position (e.g., posture) when determining the estimated levels of analytes.

Referring to FIG. 1, an example system 100 is shown for obtaining and processing electrocardiogram (ECG) data from a patient 102. The system 100 includes multiple components, and in some implementations, can be configured to carry out the computer-implemented methods and processes discussed herein. Generally, the system 100 can estimate a level of an analyte in the patient 102 based on analysis of the patient's ECG and a model that correlates characteristics of ECGs (e.g., waveform features) with levels of one or more analytes in the patient. In some implementations, the model can be personalized to the particular patient 102. In some implementations, the model can be based on correlations measured for a population of patients other than or in addition to the particular patient 102. The system 100 is also operable to monitor a patient's position and to adjust the analysis for determining an analyte level based on the patient's position, due to changes that can result in the patient's ECG when the patient's position is offset from an initial, baseline position.

In the setup of FIG. 1, the ends of a set of leads 104 are physically connected to the patient 102. The set of leads 104 can be connected to the patient so that respective electrodes at a terminal end of each lead 104 is caused to contact a surface of the patient 102 (e.g., directly contact the patient's skin or indirectly contact the patient through a garment). In some implementations, the set of leads 104 can be provided in a patch that can be quickly and easily attached to the patient (e.g., via adhesive between a patient-facing surface of the patch and the surface of the patient).

The leads 104 can also be arranged relative to each other on the patch in a particular geometric pattern (e.g., in a circular or rectangular pattern). As explained further below, by spacing the leads 104 so that the electrodes are distributed over a two-dimensional area on the surface of the patient 102, different ECG vectors can be computed among the signals sensed by different leads, where each of the ECG vectors provides a different representation of the patient's physiological electrical activity resulting from differences in the sensing locations of the electrodes/leads. For example, different positions, distances, angles, or a combination of these, among electrodes affixed to the patient may result in somewhat different ECG vectors for the same beats. In some implementations, an ECG vector can be computed by taking the difference between the electrical signal sensed by the electrode of a first of the leads 104 and the electrical signal sensed by the electrode of a second of the leads 104. In some implementations, all or some of the leads may be placed in the patient 102 subcutaneously.

In some implementations, multiple independent ECG sensing devices can be deployed on the patient 102. For example, a multi-polar patch having leads for a first set of electrodes may be affixed to the patient at a first location area, and a bipolar patch having a pair of electrodes may be affixed to the patient at a second location area. The multipolar patch and the bipolar patch may be physically distinct from each other, but both may be used concurrently to sense and record ECG data for the patient 102. In some implementations, the data recorder and control unit 110 and/or the ECG processing system 112 can normalize the signals from each of multiple independent ECG sensing devices and can synchronize the signals, e.g., so that the same beats from the patient 102 may be correlated signals recorded from each of the sensing devices.

Synchronization may be carried out, for example, by correlating times at which the signals were recorded, by aligning segments or features of individual beats represented in the signals, or both. In some examples, signals among independent sensing devices can be actively synchronized by use of a beacon that transmits radio frequency (RF) or audio signals for zeroing a real-time clock on each of the sensing devices. The signals from each of the devices can then be tagged with timestamps indicated by the respective clocks on the devices, thereby enabling synchronization via the timestamps. In other examples, a beacon generated from an external device or from within one or more of the sensing devices may be transmitted for reception by the sensing devices. The interval between transmitted beacons may be random, but each time a beacon is received, a sensing device may mark the ECG signal from the sensing device within an indication of the received beacon. The random intervals create a pattern that can be matched among each of the sensing devices to thereby synchronize the ECG signals from each device.

In some implementations, ECG signals from the sensing devices may be passively synchronized. For example, electrical activity of the patient's heart may be synchronized by autocorrelation of the RR intervals in beats of signals sensed by each of the devices. Matching PVC patterns or other ectopic beats can also be used for passive synchronization. In some implementations, baseline wandering and accelerometer data that represents identifiable patient movements (e.g., a sneeze or body position change) may be used to synchronize signals, e.g., by applying the baseline wander or accelerometer data as fiducial points for synchronization.

In some implementations, 2, 3, 4, 5, or more independent sensing devices may be coupled to a patient for concurrent data collection and processing.

The patient 102 can also be adorned with a set of one or more orientation/motion sensors 106. An orientation/motion sensor 106 is generally a transducer that generates an electrical signal representing at least one of an orientation or a movement (e.g., acceleration) of the sensor 106. When such a sensor 106 is affixed to the patient 102, the sensor can generate an electrical signal representing at least one of an orientation or a movement (e.g., acceleration) of the patient 102. Examples of orientation/motion sensors 106 include an accelerometer, a gyroscope, a gravity sensor, a magnetometer, a compass, or a rotational vector sensor. The set of orientation/motion sensors 106 can be directly or indirectly connected to the patient 102, e.g., via a garment or a band that is worn by the patient 102. In some implementations, the orientation/motion sensors 106 are provided in a device (e.g., a patch) that is distinct from a device (e.g., a patch) that includes the ECG leads 104. In some implementations, the orientation/motion sensors 106 can be integrated into a same device (e.g., a patch) that includes the ECG leads 104. In some implementations, the system 100 may use orientation/motion data characterizing signals sensed by sensors in users' portable consumer devices such as a smartphone 108 (e.g., that the user holds while an ECG is performed) or a wearable device having orientation/motion sensors (e.g., a smartwatch).

Information representing the signals sensed by the ECG leads 104 and the orientation/motion sensors 106 are communicated (e.g., by physical wired connection or by a wireless data connection) to a data recorder and control unit 110. The data recorder and control unit 110 is a computing device that receives information directly from the input sensors and provides data corresponding to the received information to ECG processing system 112. The data recorder and control unit 110 may, for example, include analog circuitry that performs amplification and filtering of the signals from the sensors 104, 106 connected to the patient. The unit 110 may also include an analog-to-digital converter that generates digital samples for processing by the ECG processing system 112. Additionally, the data recorder and control unit 110 can include multiple channels that allow it to concurrently receive, process, and transmit signals corresponding to each of the leads 104 and each of the orientation/motion sensors 106. In some implementations, the data recorder and control unit 110 is a standalone device. In some implementations, the data recorder and control unit 110 can be integrated as one or more components within the ECG processing system 112.

Next, the ECG processing system 112 is a computing system that is programmed to process ECG data and orientation/motion data from the data recorder and control unit 110, and based on such data, to monitor a position of the patient 102 and determine estimated levels of one or more analytes present in the patient 102. The ECG processing system 112 can present information concerning estimated levels of analytes on an electronic display 114*a* (e.g., LCD monitor). The system 112 also receives user input via one or more peripherals, such as a keyboard 114*b*. In some implementations, the ECG processing system 112 may be implemented in a clinical setting on one or more computers operated by a healthcare organization. In some implementations, the ECG processing system 112 may be implemented on a personal user device of the patient 102, such as a desktop or notebook computer, a mobile device (e.g., a smartphone or tablet computing device). In some implementations, ECG processing system 112 may be implemented on one or more computer servers that provide a cloud-based service for processing ECG data and estimating analyte levels based on ECG data. In some implementations, the ECG processing system 112 processes data and outputs results in real-time, e.g., as the ECG is performed on the patient 102. In some implementations, the ECG processing system 112 accesses pre-stored data (e.g., as recorded and stored on the data recorder and control unit 110) and analyzes the data to determine estimated levels of analyte in a patient after the ECG has been performed.

The ECG processing system 112 can include components 116-132, as shown in FIG. 1, or a subset thereof. Generally, each of the components 116-132 can be implemented by a combination of computer hardware and software that are configured to perform the operations described herein.

To begin, the input signal conditioner 116 performs preprocessing operations on data received from the data recorder and control unit 110. For example, the received data may be filtered, normalized, or averaged, and "bad" data may be discarded (e.g., data that is excessively noisy). The input signal conditioner 116 further generates, for each possible combination of lead pairs from the leads 104, an ECG vector that represents the electrical activity for one or more beats of the patient 102 according to a difference between the signals sensed by the respective electrodes for the given lead pair.

Next, the QRS detector and features analyzer 118 processes ECG data outputted by the input signal conditioner 116. For each ECG vector corresponding to the different lead pairs, the analyzer 118 identifies the segment of the ECG vector corresponding to the QRS-complex, and then determines a set of one or more features that characterize the QRS-complex. Thus, the analyzer 118 determines multiple sets of QRS features, each set characterizing the QRS-complex of the respective ECG vector for a different lead pair. In some implementations, the QRS features can be extracted using neural networks, e.g., one or more recurrent and/or convolutional neural networks. Examples of QRS features that the analyzer 118 may derive include peak amplitude of any of the Q-, R-, or S-waves, total area of the QRS-complex, area of any of the Q-, R-, or S-waves, left or right slopes of any of the Q-, R-, or S-waves, ratio of the areas of any of the Q-, R-, or S-waves, centers of gravity of the QRS-complex as a whole or of any of the Q-, R-, or S-waves, or a combination of these. In some implementations, the features of the QRS-complexes can be determined after time-warping to normalize the time-width of the QRS-complexes (e.g., so that the time interval from beginning to end of each of the QRS-complexes is uniform).

The ECG processing system also includes a baseline QRS model 120. The baseline QRS model 120 stores a baseline set of waveform features (e.g., features of a baseline QRS-complex). The baseline set of waveform features can be generated by the system 112 at particular times in which the patient 102 is known to be in a pre-defined position (e.g., in a stationary, upright, and standing position; in a stationary, upright, and sitting position; or in a stationary position lying down). The pre-defined position may be, for example, a default position or the same position that the patient 102 was in when a "best" lead pair was selected as a baseline by a healthcare professional due to that lead pair's ability to generate an ECG vector having waveform features that accurately correlate with estimated levels of one or more analytes for the patient. Thus, when the patient 102 is determined to be in the pre-defined position, the ECG processing system 112 may generate an ECG vector based on ECG data corresponding to a time interval in which the patient 102 is in the pre-defined position. The system 112 may then identify the QRS-complex from the baseline ECG vector, derive a baseline set of QRS features from the baseline ECG vector, and stores the baseline set of features (and generally any other data characterizing the QRS-complex of the baseline ECG vector) in the baseline QRS model 120. In some implementations, the baseline set of QRS features is automatically updated each time the patient 102 is determined to return to the pre-defined baseline position. For example, an ECG patch and accelerometers may be worn by the patient on a constant basis throughout a day. The patient is therefore likely to be moving around significantly over this period of time. Because the baseline ECG vector may change significantly over time (e.g., resulting from movement of the ECG patch or changing body positions), the baseline QRS model is automatically updated in response to detected events and/or periodically. Moreover, when the patient is in the pre-defined position, the pre-selected baseline lead pair is more likely to be located the same distance and angle relative to the patient's heart or other organs as when the baseline lead pair was validated for reliably predicting the level of analyte in the patient.

The patient position and movements monitor 122 monitors a data stream relating to the orientation and/or motion of the patient 102 during the course of an ECG session, and determines positions of the patient 102 at particular times during the course of the ECG session. In some implementations, the patient position and movements monitor 122 monitors orientation/motion data that stems from signals generated by the orientation/motion sensors 106, analyzes the data to determine a current position of the patient 102 (e.g., by feeding the orientation/motion data to a classifier), and generates an alert each time the patient's current position is determined to match the pre-defined position. The alert from the patient position and movements monitor 122 can cause the ECG processing system 112 to trigger an update of the baseline QRS features represented by the baseline QRS model 120. It should be understood that the monitor 122 may allow for some tolerance between the actual (measured) position of the patient 102 and the pre-defined baseline position when determining whether the actual position matches the pre-defined baseline position. For example, the monitor 122 may consider the patient's actual position to match the pre-defined baseline position if the actual position of the patient is within 5-percent or 10-percent of a center of the pre-defined position (e.g., the pre-defined position may encompass a range of positions that vary from a center position).

In some implementations, the patient position and movements monitor 122 may determine the position of a patient using input data other than orientation/motion data. For example, the system 112 may simply prompt the patient 102 that he or she is in the baseline position, and if the patient 102 verifies that he or she is in the baseline position, then the system 112 can take appropriate action, such as updating the baseline QRS features in the model 120. In some implementations, the system 112 may use image or video data from a camera to recognize the patient's position.

The ECG processing system 112 can further include a dynamic lead selector 124. The dynamic lead selector 112 is generally configured, when the patient position and movements monitor 122 indicates that the patient 102 is not in the baseline position, to designate one or more of the lead pairs as proxy lead pairs. The dynamic lead selector 112 selects proxy lead pairs from among the set of lead pairs for which the QRS detector and features analyzer 118 generated a respective ECG vector and a corresponding set of waveform features (e.g., QRS features). In some implementations, the one or more proxy lead pairs are selected based on a level of similarity between the respective sets of waveform features for the proxy lead pairs and the baseline set of waveform features indicated by the baseline QRS model 120. For example, the dynamic lead selector 112 may compare the QRS-features of the respective ECG vector for each available lead pair with the baseline QRS-features. The top n lead pairs having QRS-features that most closely match the baseline QRS-features can be selected and designated as proxy lead pairs (where n is 1, 2, 3, 4, 5, or another integer>=1). In some implementations, the dynamic lead selector 124 scores the similarity between waveform features of available lead pairs and the baseline waveform features using a correlation function.

Upon selection of the proxy lead pairs, the dynamic lead selector 112 selects or generates a proxy ECG vector based on the respective ECG vectors that correspond to the proxy lead pairs. A "proxy" ECG vector refers to the ECG vector that that the processing system 112 analyzes to derive an estimated analyte level for a patient. When the patient 102 is in the pre-defined position, a "proxy" ECG vector is not needed, because the system 112 analyzes the ECG vector corresponding to the pre-selected baseline lead pair to determine estimated analyte level. However, when the patient 102 is out of the pre-defined position, the ECG vector corresponding to the pre-selected baseline lead pair may no longer be as reliable to generate an accurate estimation of the patient's analyte level; therefore, the system uses a proxy ECG for analysis based on the ECG vectors from one or more proxy lead pairs having waveform features that most closely match a baseline. For example, if the dynamic lead selector 112 designates just a single proxy lead pair, then the corresponding ECG vector for the designated lead pair can be used as the proxy ECG vector. In instances where the dynamic lead selector 112 designates multiple proxy lead pairs, the dynamic lead selector 112 can generate a proxy ECG vector as a combination of the respective ECG vectors for each of the multiple proxy lead pairs (e.g., by averaging the respective ECG vectors for each of the multiple proxy lead pairs).

The T-wave detector and features analyzer 126 analyzes a proxy ECG vector, determines a representative beat from the proxy ECG vector, automatically identifies a T-wave in the representative beat from the proxy ECG vector, and computes a set of one or more features of the identified T-wave. As discussed below, the features of the T-wave can be correlated with analyte levels of the patient and used to determine an estimated level of one or more analytes presently in the patient. In some implementations, the ECG vector may only contain ECG data spanning a single beat, in which case that beat is used as the representative beat. In some implementations, the ECG vector may contain ECG data spanning multiple beats of the patient 102, in which case the representative beat can be selected from among the multiple beats (e.g., based on noise or quality scores of the beats) or can be generated by averaging or otherwise combining two or more of the multiple beats. The set of T-wave features that the analyzer 126 computes can include one or more of a left slope of the T-wave, a right slope of the T-wave, an area of the T-wave, an amplitude of the T-wave, an interval of the T-wave from beginning to end, a center-of-gravity of the T-wave, or a center-of-gravity of a portion of the T-wave (e.g., first or last quarters of the T-wave). Some of these features are illustrated in FIG. 2, for example.

The ECG processing system 112 can further include an ECG-analyte model 128. This model 128 correlates ECG waveform features (e.g., T-wave features) with levels of analytes in a patient. The model 128 can include functions from which an estimated analyte level can be derived given a set of T-wave features and/or can include a set of sample data points that correlate different sets of ECG features with analyte levels. In some implementations, the model 128 can be personalized to the patient 102 based on data that correlates actual analyte levels in the patient (e.g., determined via a blood test) with T-wave features seen at the time the analyte levels were measured. In some implementations, the model 128 may be derived based on data from a population of users that may or may not include the patient 102. Further discussion about estimating analyte levels based on ECG data is provided in PCT Publication No. WO2015/048514, a publication of PCT Application US2014/057811, filed Sep. 26, 2014, which is hereby incorporated by reference in its entirety. The analyte level estimation module 130 is operable to query the ECG-analyte model 128, including providing the set of T-wave features for the proxy ECG vector to the model 128. In response to the query, the analyte level estimation module 130 obtains a value indicative of the estimated level of the analyte in the patient during the relevant time.

A notifications manager 132 of the ECG processing system 112 is programmed to output information about the estimated level of an analyte in a patient, as determined by the estimation module 130. The notifications manager 132 may, for example, display a representation of the estimated analyte level on display 114a and may store the estimated level in a log maintained by the system 112. In some implementations, the notifications manager 132 may generate alerts for presentation to a user (e.g. to the patient 102 and/or the patient's doctor) if the estimated level of an analyte is determined be outside a pre-defined range of acceptable levels. Thus, if the patient's analyte level is determined to be unduly low or high, an alert can be generated so that further investigation or remedial action can be performed.

Figure 2:
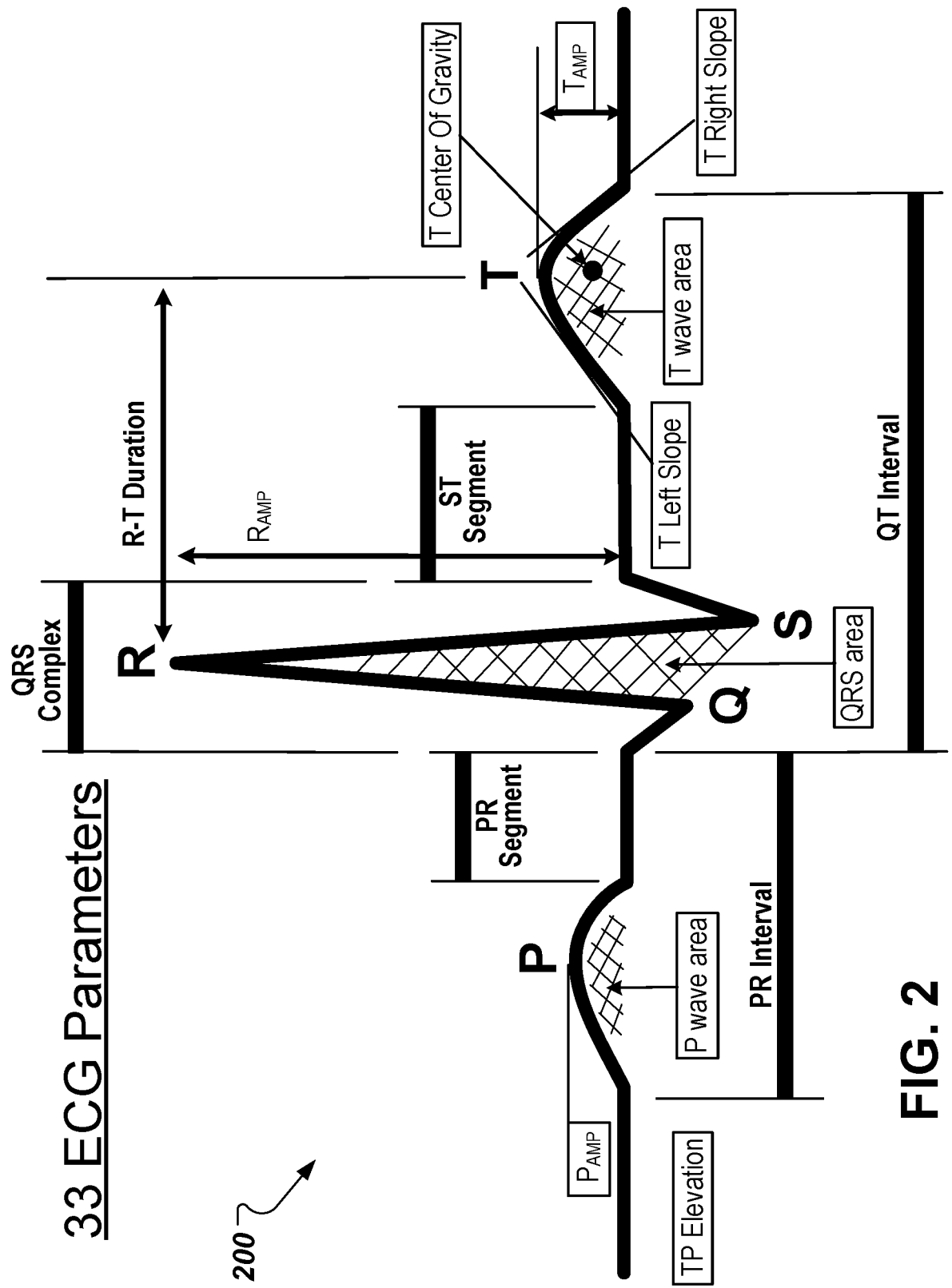
FIG. 2 is a diagram of an example ECG tracing for one heartbeat of a patient. The ECG tracing shows constituent segments of the beat and various waveform features (e.g., parameters).

FIG. 2 is a diagram of an example tracing 200 of an ECG vector for one heartbeat of a patient. The ECG tracing shows constituent segments of the beat and various waveform features (e.g., parameters). Among the beat segments shown in the tracing 200 are a P-wave, a QRS-complex (comprising a Q-wave, R-wave, and S-wave), and a T-wave. Various waveform features are also represented in the figure, such as areas of waves, time intervals between various points in the beat within and between different waves, centers of gravity of waves, amplitudes of the waves, and slopes of particular portions of the waves. As discussed with respect to FIGS. 1 and 4-6, a computing system may determine waveform features and use the features to determine estimated analyte levels in a patient and to determine a proxy ECG vector given a position of a patient.

Figure 3:
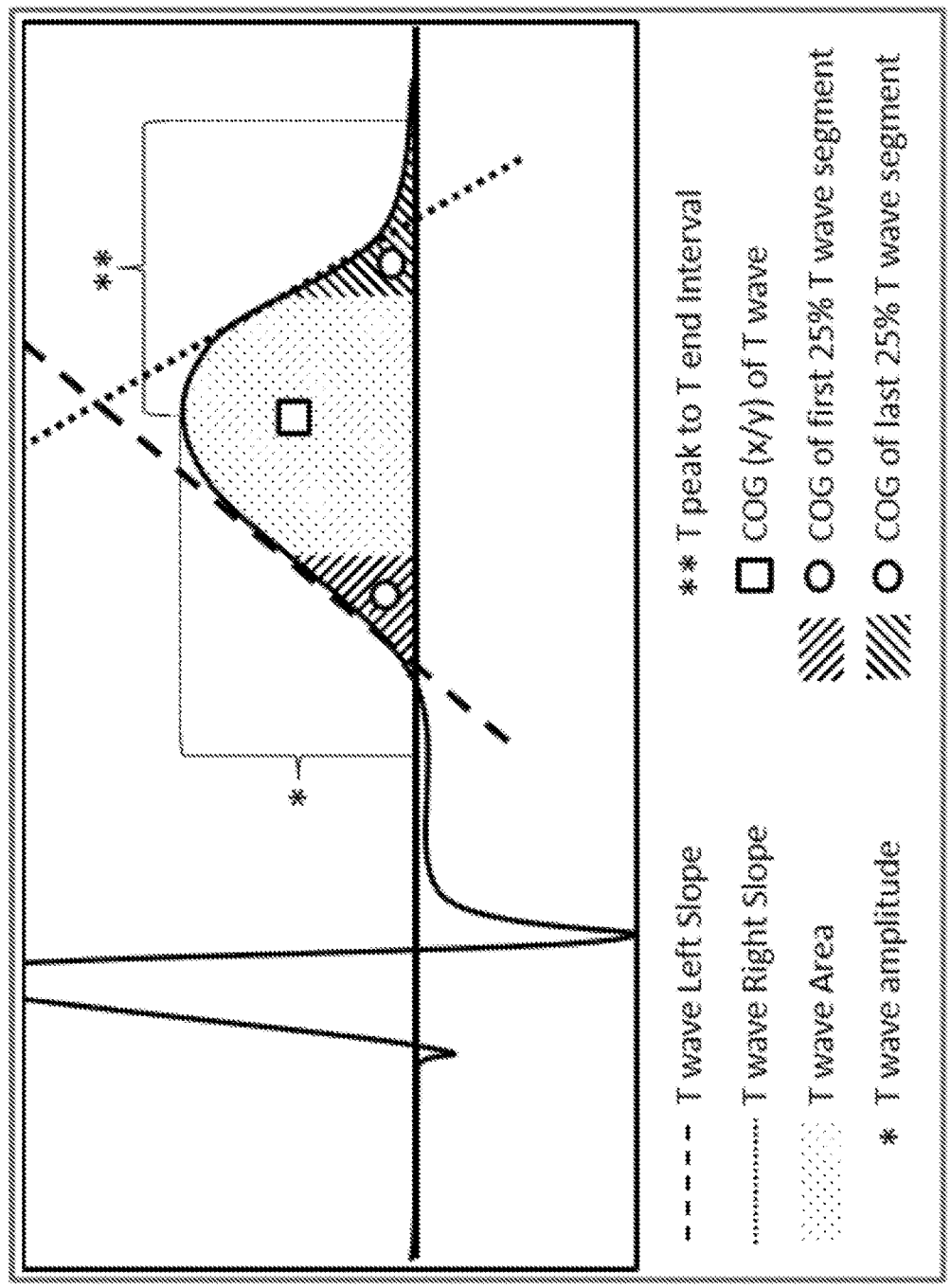
FIG. 3 is a diagram of another example ECG tracing for one beat of a patient. The diagram includes markings representing features of a T-wave shown in the ECG tracing.

FIG. 3 is a diagram of another example tracing 300 for one beat from an ECG vector of a patient. The diagram includes markings representing features of a T-wave shown in the ECG tracing 300, including T-wave left slope, T-wave right slope, T-wave area, T-wave amplitude, T-peak to T-end interval, a center-of-gravity of the T-wave, and centers-of-gravity of the first and last quarters of the T-wave. As discussed with respect to FIGS. 1 and 4-6, a computing system may analyze an ECG vector of a beat to determine T-wave features and use the features to generate an estimated level of analyte in a patient.

Figure 4:
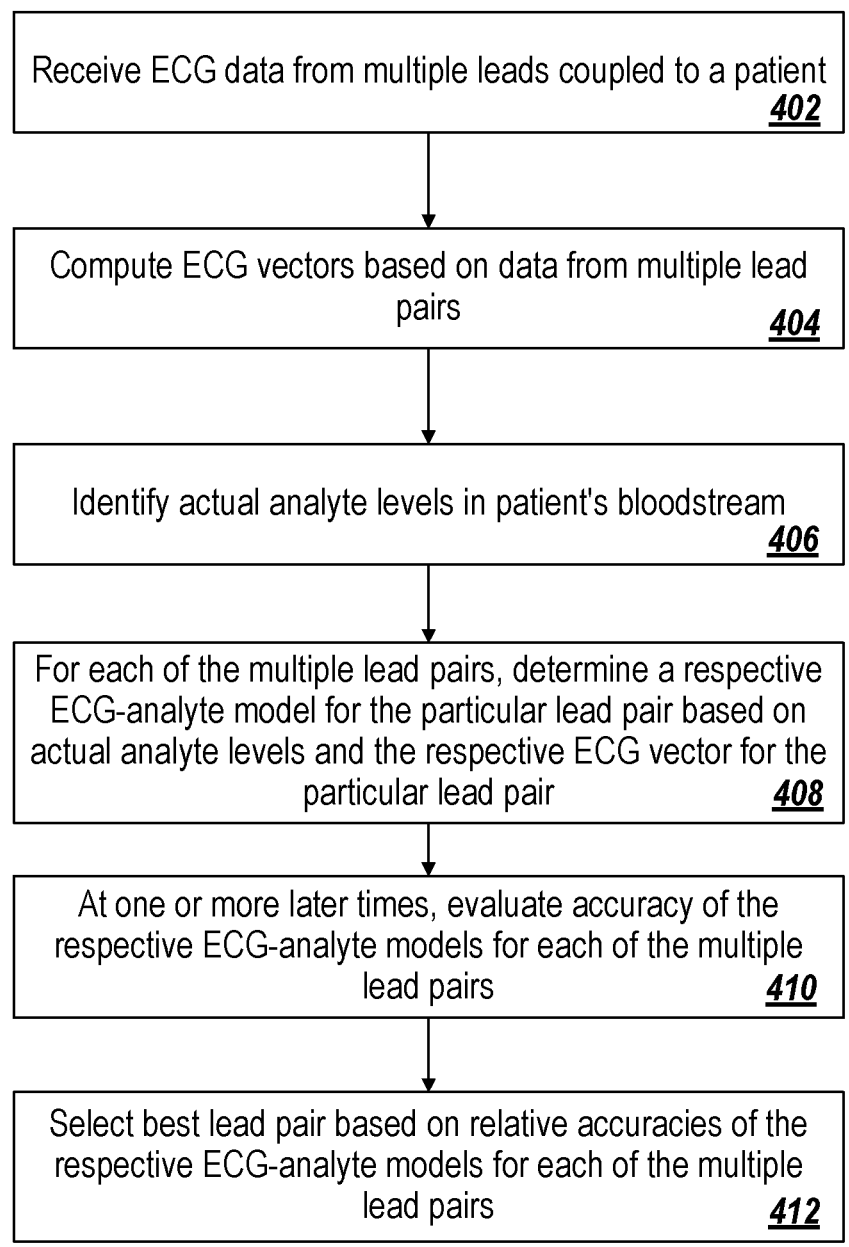
FIG. 4 depicts a flowchart of an example process for selecting a baseline pair of ECG leads from which to derive an ECG vector and baseline waveform features when a patient is determined to be in a pre-determined baseline position.

FIG. 4 depicts a flowchart of an example process 400 for selecting a baseline pair of ECG leads from which to derive an ECG vector and baseline waveform features when a patient is determined to be in a pre-determined baseline position. The process 400 may be carried out by a computing system, e.g., an ECG processing system.

At stage 402, the system obtains respective sets of ECG data for multiple leads coupled to a patient. The respective sets of ECG data can each represent physiologic electrical activity of the patient during the same period of time, but from different locations of the patient to which terminal electrodes on the lead were attached. The ECG data obtained at this stage 402 is obtained while the patient is in a pre-determined baseline position (e.g., stationary, upright, and standing; stationary, upright, and sitting; stationary and lying down).

At stage 404, the system computes ECG vectors corresponding to different combinations of lead pairs. For example, the system may have received respective sets of ECG data from each of 4 leads connected to a patient. Six permutations of lead pairs are possible from the 4 leads (e.g., L1-L2, L1-L3, L1-L4, L2-L3, L2-L4, and L3-L4), and the system may generate an ECG vector for each lead-pair permutation by taking the difference in the signals represented by the ECG data for the particular leads in each pair.

At stage 406, the system obtains data that represents actual levels of an analyte in the patient (e.g., as measured by two or more blood tests). At stage 408, the system then creates, for each of the possible lead-pairs, a respective ECG-analyte model for the respective lead-pair. The model for a given lead pair is created by correlating ECG waveform features (e.g., T-wave features) of a representative beat from the ECG vector for that lead pair with the data that represents actual levels of the analyte in the patient when the patient is in the baseline position. Later (e.g., in subsequent days or weeks), the system evaluates the accuracies of the respective models for each of the lead-pairs (stage 410). For example, the patient may return to a clinic and have their blood drawn for a direct measurement of the amount of analyte (e.g., potassium) present in the blood. The patient's ECG can be taken at or around the same time as the blood test while the patient is in the baseline position. The system can then apply the models for each of the lead-pairs to determine an estimated level of the analyte present in the patient. At stage 412, the system designates the best-performing lead pair as the baseline lead pair for subsequent use in generating baseline ECG vectors and waveform features when the patient is in a baseline position. The best-performing lead pair may be, for example, the lead pair whose corresponding model best predicted the actual level of analyte present in the patient using ECG data from the leads in that lead pair.

Figure 5:
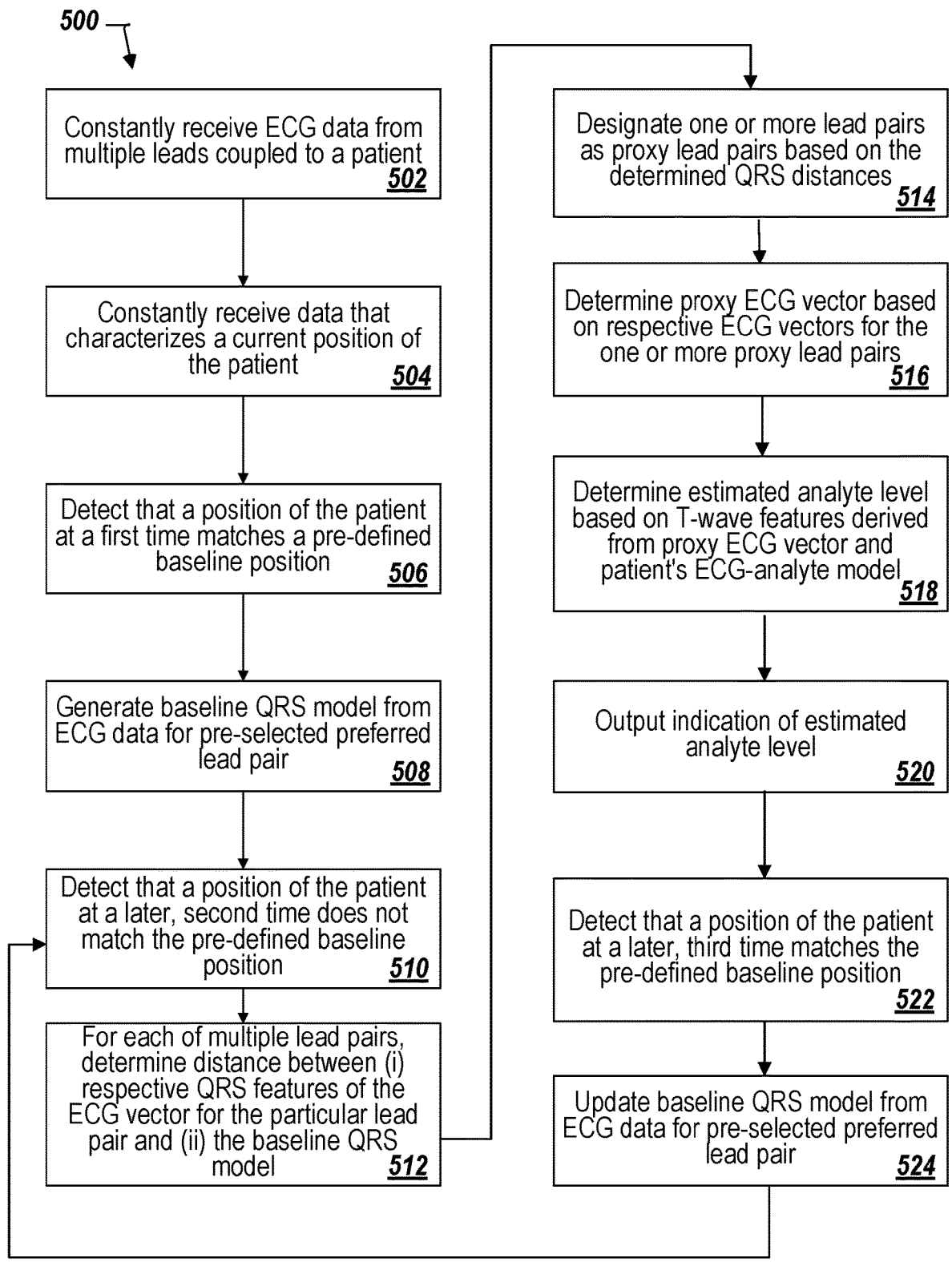
FIG. 5 depicts a flowchart of an example process for estimating a level of an analyte in a patient, while accounting for a change in a patient's position from a baseline position.

FIG. 5 depicts a flowchart of an example process 500 for estimating a level of an analyte in a patient, while accounting for a change in a patient's position from a baseline position. The process 500 may be carried out by an ECG processing system, e.g., ECG processing system 112 of FIG. 1.

At stage 502, the system obtains respective sets of ECG data for multiple leads coupled to a patient. The respective sets of ECG data can each represent physiologic electrical activity of the patient during the same period of time, but from different locations of the patient to which terminal electrodes on the lead are attached. The data may be stored from a previously performed ECG session, or may be received streaming in real-time as an ECG session is ongoing. Along with the ECG data, the system also receives data that characterizes a position of the patient at times that are synchronized with times of the ECG data. Thus, the system may correlate a patient's position at a given time with ECG vectors at that time. In some implementations, the system receives orientation and/or motion data of the user sensed by an orientation/motion sensor, and the system processes the orientation/motion data to determine the position of the patient.

At stage 506, the system detects that the position of the patient at a first time matches a pre-defined baseline position. In response, at stage 508, the system generates a baseline QRS model from ECG data for the designated baseline lead-pair. For example, the system may compute an ECG vector for the baseline lead-pair during the first time interval, determine a representative beat from the ECG vector, identify the QRS-complex in the representative beat, and determine a set of features for the QRS-complex. The set of features may be stored in the baseline QRS model.

At stage 510, the system later detects that the position of the patient at a second time does not match the pre-defined baseline position (e.g., the patient has moved out of the baseline position). In response to identifying that the patient is no longer in the baseline position, the system at stage 512 determines respective sets of waveform features (e.g., features of the QRS-complex) for representative beats from ECG vectors corresponding to each of a set of candidate lead pairs. For example, for each candidate lead pair, the system computes an ECG vector for the candidate lead pair during the second time interval, determines a representative beat from the ECG vector, identifies the QRS-complex in the representative beat, and determines a set of features for the QRS-complex.

At stage 514, the system designates one or more of the candidate lead pairs as proxy lead pairs. The proxy lead pairs can be selected from among all the candidate lead pairs based on levels of similarity determined between the respective sets of waveform features that correspond to each of the candidate lead pairs and the baseline waveform features (e.g., baseline QRS features) indicated by the baseline QRS model. For example, the top 1, 2, or 3 (or another number n) of the candidate lead pairs can be designated proxy lead pairs. At stage 516, the system determines a proxy ECG vector based on the ECG vectors corresponding to the proxy lead pairs. If there is just one proxy lead pair, then that lead pair's corresponding ECG vector can be used as the proxy lead pair. If multiple proxy lead pairs have been designated, then an average or other combination of the ECG vectors for each of the proxy lead pairs can be determined as the proxy ECG vector.

At stage 518, the system determines an estimated level of an analyte in the patient. In some implementations, the estimated level of the analyte is determined by identifying a representative beat in the proxy ECG vector, identifying the T-wave in the representative beat, determining a set of T-wave features that characterize the T-wave, and applying a model to the set of T-wave features to generate the estimated level of the analyte. The model is generally configured to correlate T-wave features with levels of analyte in a patient. At stage 520, the system outputs an indication of the estimated analyte level, e.g., by displaying a representation of the level to a patient or a healthcare professional.

At stage 522, the system continues to monitor the position of the patient during an ongoing ECG session. During this monitoring, the system detects that the patient has returned to the pre-defined baseline position. In response, the system updates the baseline QRS model, e.g., by computing the ECG vector for the designated baseline lead pair, determining a representative beat from this ECG vector, identifying a QRS-complex in the representative beat, and storing features of the QRS-complex in the updated baseline model. The updated model can subsequently be used during the ongoing ECG session the next time an estimated analyte level is to be determined when the patient is not in the baseline position. Thus, the process 500 can return from stage 524 to stage 510.

FIG. 6 depicts a flowchart of an example process 600 for estimating a level of an analyte in a patient using waveform features from a selected ECG vector. The process 600 may be carried out by an ECG processing system, e.g., ECG processing system 112 of FIG. 1. Generally, the process 600 may be performed when orientation and/or motion data of the patient is not available or the position of the patient cannot otherwise be determined. The process 600 may also be advantageous to select a representative beat from the ECG vector for a given lead pair, including in instances where ECG data is available from only one lead pair.

At stage 602, the system obtains a baseline QRS model that characterizes baseline QRS features of a QRS-complex in a representative beat from an ECG vector for a particular lead pair. At stage 604, the system monitors data sensed by one or more lead pairs, including the particular lead pair. QRS-features derived from ECG vectors for each of the monitored lead pairs can be compared to the baseline QRS features. At stage 606, the system selects a particular representative beat having QRS-features that best match the baseline QRS features. At stage 608, the system determined an estimated level of an analyte in the patient based on T-wave features derived from a T-wave in the representative beat selected at stage 606. Finally, at stage 610, the system outputs and indication of the estimated analyte level.

Figure 7:
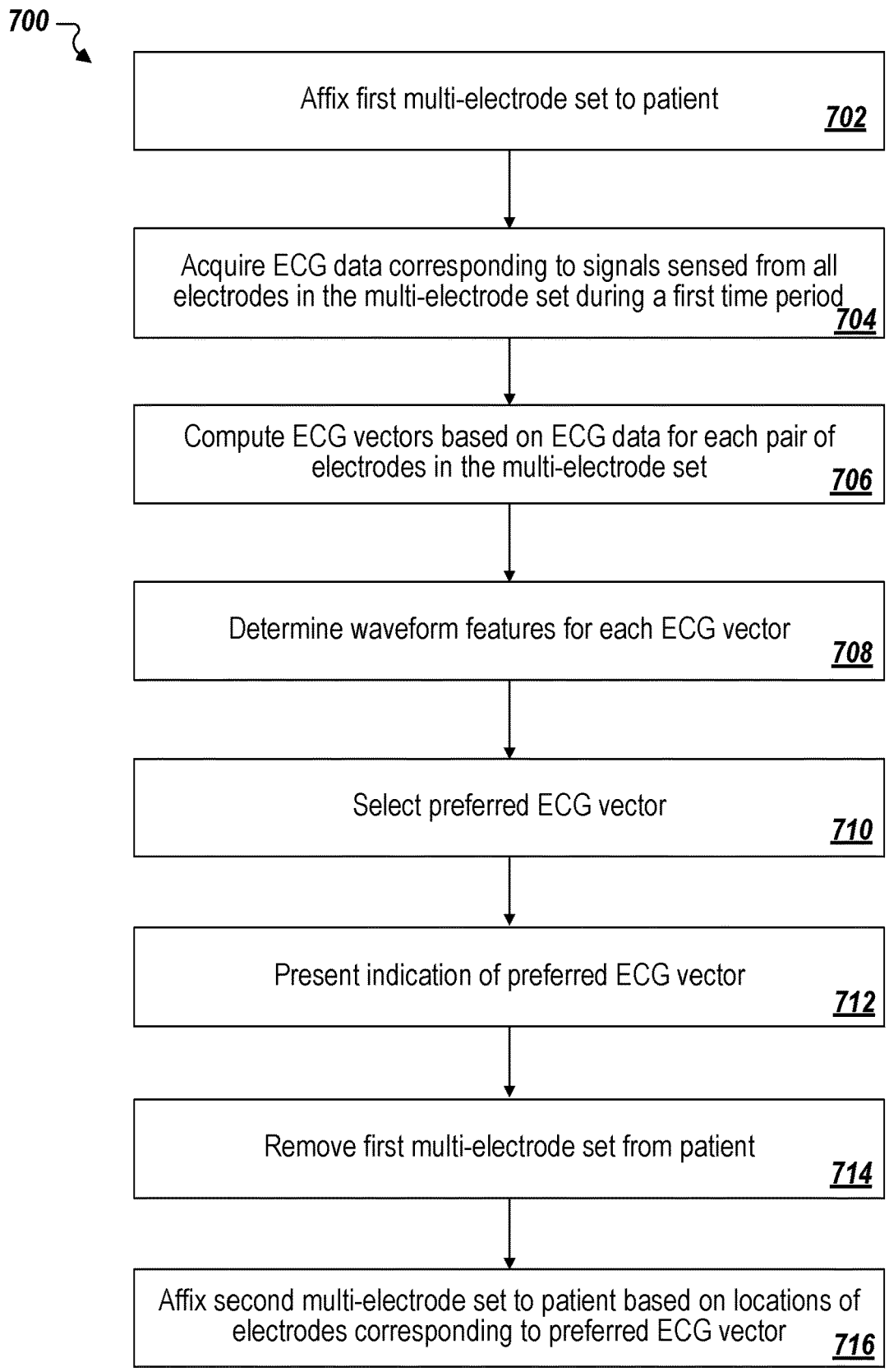
FIG. 7 depicts a flowchart of an example process for using a multi-electrode pre-placement tool to determine, for example, a preferred placement (e.g., location and orientation) of a bipolar electrode device on a patient.

FIG. 7 is a flowchart of an example process 700 for using a pre-placement electrode device having a first set of multiple electrodes (e.g., a multi-polar device) to determine a preferred placement of a second electrode device having two or more electrodes (e.g., a bipolar device). In some implementations, the pre-placement electrode device has a greater number of electrodes than the second electrode device so that the first set of electrodes can provide a set of candidate ECG vectors to guide placement of the second electrode device on the patient. Based on analysis of ECG vectors resulting from use of the pre-placement device, a preferred ECG vector can be automatically selected, and the second electrode device is then placed on a patient such that a location and/or orientation of a pair of electrodes from the second device matches a location and/or orientation of a pair of electrodes from the pre-placement device on the patient that corresponds to the preferred ECG vector. As one example, the pre-placement electrode device may therefore be used to determine an optimal placement of a bipolar electrode device on a patient.

At stage 702, a first set of multiple electrodes is affixed to a patient. The first electrode set is generally arranged for temporary use on the patient, e.g., as a pre-placement tool in a procedure for guiding placement of a second set of multiple electrodes that will be affixed to the patient for more sustained use. In some implementations, the first electrode set is integrated into a single device (e.g., a patch) and the electrodes in the first set may be held in fixed positions relative to each other. The electrodes may be arranged in a circular or other geometric pattern. In other implementations, all or some of the electrodes in the first set may be arranged independently of each other, so that each electrode can be selectively placed at a desired position on the patient. The first electrodes may be glued or otherwise held in contact with the patient, and may be placed cutaneous on the patient's skin, or may be placed subcutaneously. The first electrodes are generally configured to sense physiological electrical signals of the patient, such as ECG signals. Generally, the first set of electrodes may have any number of electrodes sufficient to provide multiple ECG vectors, e.g., in the range of 3-12 electrodes.

At stage 704, a computing system acquires ECG data corresponding to signals sensed by the first set of multiple electrodes during a defined period of time. For example, signals from each of the electrodes may collected, pre-processed, (e.g., filtered, amplified, digitized) and stored by the computing system. The signals may represent levels of the physiological electrical activity of the patient as a function of time over the defined period of time. The defined period of time may be selectable by a user. In some examples, the defined period of time is in a range of 5-10 seconds, 10-15 seconds, 15-20 seconds, 20-25 seconds, 25-30 seconds, 30-35 seconds, 35-40 seconds, or 40-45 seconds. In some implementations, the computing system may synchronize the signals from each of electrodes, e.g., so that beats can be correlated between each of the signals.

At stage 706, the computing system computes a respective ECG vector for each pair of electrodes in the first set. In some implementations, the ECG vector for a given pair of electrodes is determined by taking the difference between the respective electrical signals sensed by the pair of electrodes, as indicated by the acquired ECG data.

At stage 708, the computing system determines values of one or more waveform features for each of the ECG vectors. In some implementations, the waveform features represent characteristics of a representative beat from the patient's ECG. The representative beat may be a particular, selected beat that occurred during the defined period of time during acquisition of the ECG data or the representative beat may be a combination (e.g., average) of two or more beats represented in the ECG data. In other implementations, final waveform feature values may be determined by statistical averaging of waveform feature values from multiple selected beats in the ECG data. Thus, multiple beats may be averaged to form a representative beat and then waveform feature values may be derived from the representative beat; alternatively, initial waveform feature values may be derived for individual beats and the values may be averaged to arrive at final waveform feature values. The waveform features may characterize aspects one or more segments of a beat, such as features of a P-wave, T-wave, or QRS-complex. Some aspects of the one or more segments that may be characterized by the waveform features include slope, area, center of gravity, peak amplitude, or energy level.

At stage 710, the computing system selects a preferred ECG vector from among the available ECG vectors stemming from the first set of electrodes. In some implementations, the preferred ECG vector is selected based on a determination that it is likely to provide the best ECG signal for use in assessing analyte levels of a patient. The preferred vector can be selected based on various criteria, including based on the waveform feature values that were derived at stage 708. For example, the preferred vector may be selected based on having a high signal-to-noise (SNR) ratio and based on the waveform feature values having desirable characteristics such as high T-wave amplitude or energy. In some implementations, the ECG vector that has the highest T-wave energy or amplitude may be selected as the preferred vector. In some implementations, a user may review a report of the waveform feature values and may provide input to the computing system to select the preferred vector.

At stage 712, the computing system automatically generates a presents to a user a notification of the preferred ECG vector. The notification may take a variety of forms and may be presented visually, aurally, or both. In one example, the first set of electrodes may be provided in an integrated pre-placement device that includes a light emitting diode (LED) for each of the electrodes. The LEDs for the pair of electrodes that correspond to the ECG vector may be turned on, set to a particular color, or blinked as a means of indicating that the electrodes provide a preferred ECG vector. A pair of electrodes that corresponds to an ECG vector is a pair whose ECG signals were processed to compute the ECG vector, e.g., by taking a difference of the signals. In some implementations, the pre-placement device includes a liquid crystal display (LCD) screen that displays text or graphics indicating the pair of electrodes that correspond to a preferred ECG vector. In some implementations, the computing system may transmit data that identifies the pair of electrodes corresponding to the preferred ECG vector to a separate computing device (e.g., smartphone, tablet, wearable computing device, notebook computer, desktop computer) of the patient or a healthcare professional. The computing device may then process the data and display an indication of the specified pair of electrodes for the preferred ECG vector.

In some implementations, the indication of the pair of electrodes that correspond to the preferred ECG vector can be used as a guide for placing a more permanent electrode device on the patient in a location and orientation that is likely to provide a high-quality ECG signal that approximately matches the preferred ECG vector obtained from the pre-placement device. For example, the pre-placement device with the first set of electrodes may be used in a clinical or home setting to facilitate attachment of a smaller electrode device with a lighter footprint and fewer electrodes to the patient. The smaller device may be a bipolar device with just two electrodes that provide a single ECG vector when coupled to the patient. At stage 714, the pre-placement device and its first set of electrodes are removed from the patient. In some implementations, the locations of the identified pair of electrodes that correspond to the preferred ECG vector can be marked on the patient. Then, at stage 716 the second electrode device (e.g., bipolar electrode device) is placed on the patient in a position and orientation that corresponds to the identified pair of electrodes from the pre-placement device. For example, the pair of electrodes on a bipolar device may be positioned at the same locations on the patient as were the identified pair of electrodes from the pre-placement device. The bipolar electrode device can then be applied to sense physiological electrical activity of the patient and to generate signals that are processed, e.g., to assess levels of potassium or other analytes in a patient.

Figure 8:
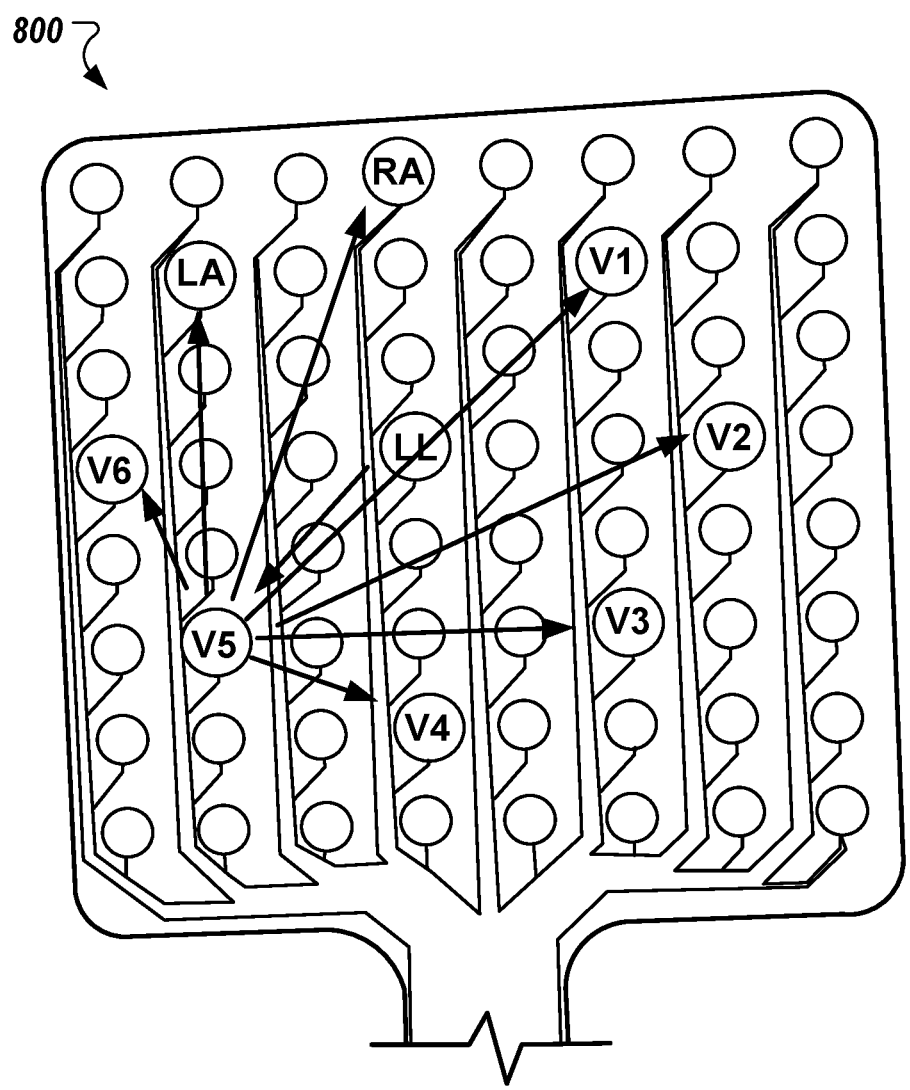
FIG. 8 is an annotated photograph of an example ECG patch having a set of electrodes arranged in a generally circular pattern.
Figure 9A:
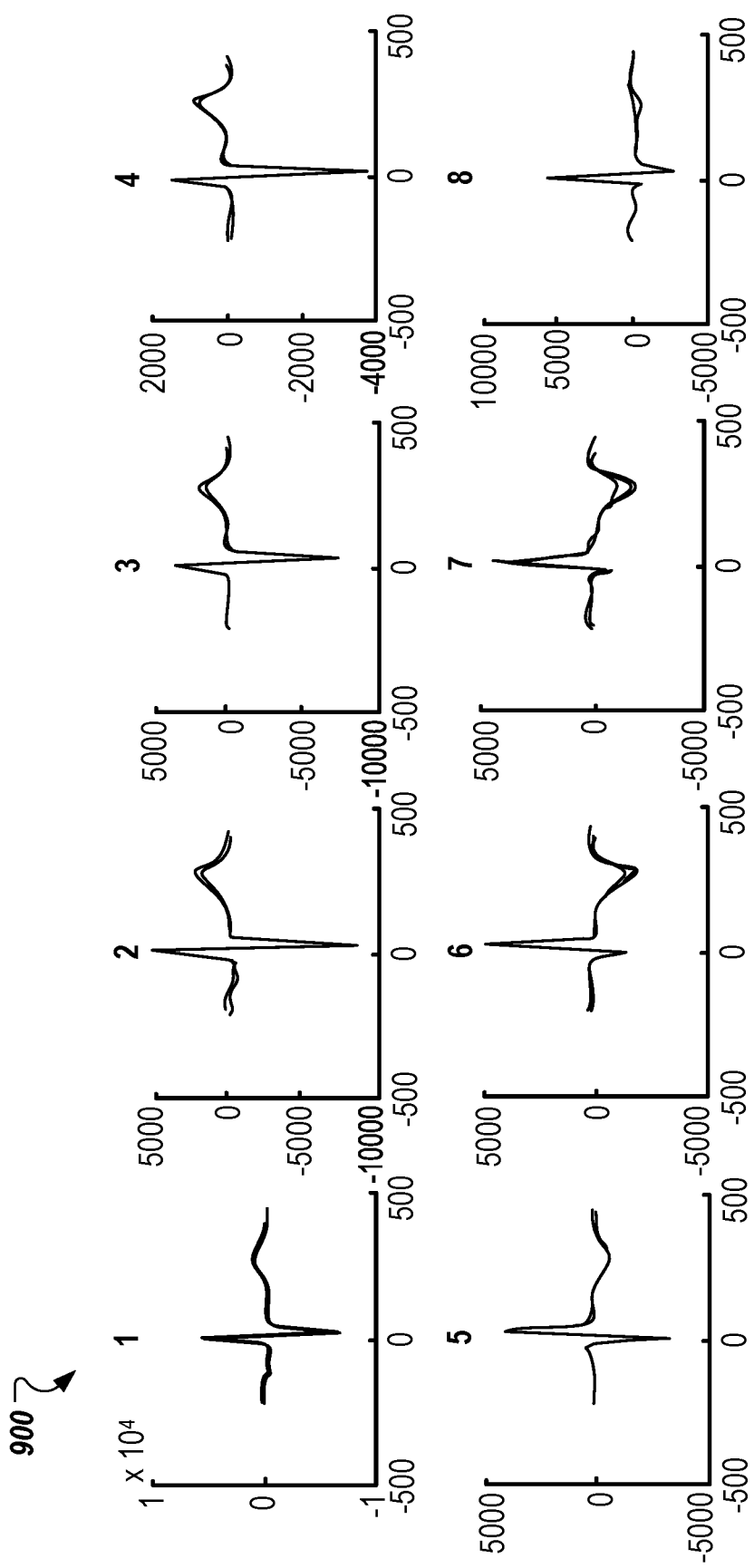
FIG. 9A shows a set of plots representing ECG vectors derived from signals sensed by different pairs of leads on the ECG patch of FIG. 8.

Referring to FIG. 8, an annotated photograph is shown of an example ECG patch 800 that includes a set of electrodes arranged in a generally circular pattern. The ECG patch include an adhesive on a substrate of the patch so that the patch may be applied and stuck to a surface of a patient, e.g., on the patient's chest. The patch in this example includes 9 leads: LA, RA, V1, V2, V3, V4, V5, V6, and LL. Eight of the leads are arranged in a generally circular pattern on the patch, with the remaining lead located in the center of the circle. As such, the various leads are capable of producing different ECG vectors by taking the difference of signals sensed by respective pairs of leads. FIG. 9A, for example, includes eight plots 900 depicting tracings of respective ECG vectors for eight different lead-pair combinations of the leads in patch 800 of FIG. 8. The ECG vectors correspond to lead pair combinations V5-RA, V5-LA, V5, LL, V5-V1, V5-V2, V5-V3, V5-V4, V5-V6. As can be seen in the various plots, the ECG vectors can vary noticeably for different lead-pair combinations.

Figure 9B:
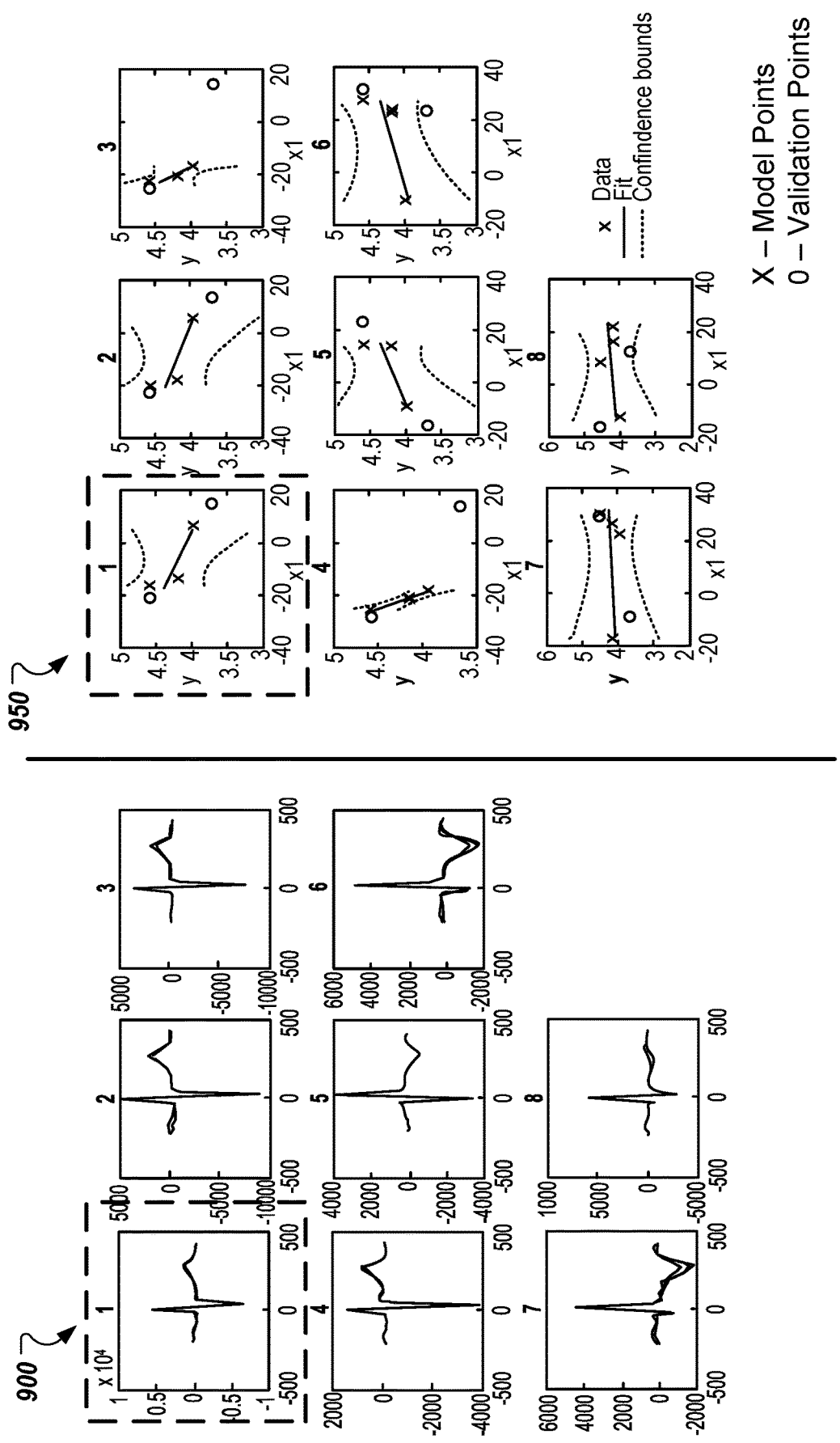
FIG. 9B shows the selection of a particular pair of leads from the ECG patch of FIG. 8 as the baseline pair of leads based on a determination that the ECG vector resulting from the particular pair of leads provides a most accurate estimation of analyte level in a patient.

FIG. 9B shows the same plots 900 (at left) in FIG. 9B, along with corresponding validation plots 950 that show, for each lead-pair, model points of estimated analyte levels and validation points of measured analyte levels. The lead-pair corresponding to plot 1 in the set of plots 900 is highlighted with the dashed box because its model best predicted the measured analyte level. In some implementations, that lead-pair can then be designated the baseline lead pair for use in subsequent determinations of estimated analyte levels.

Figure 10:
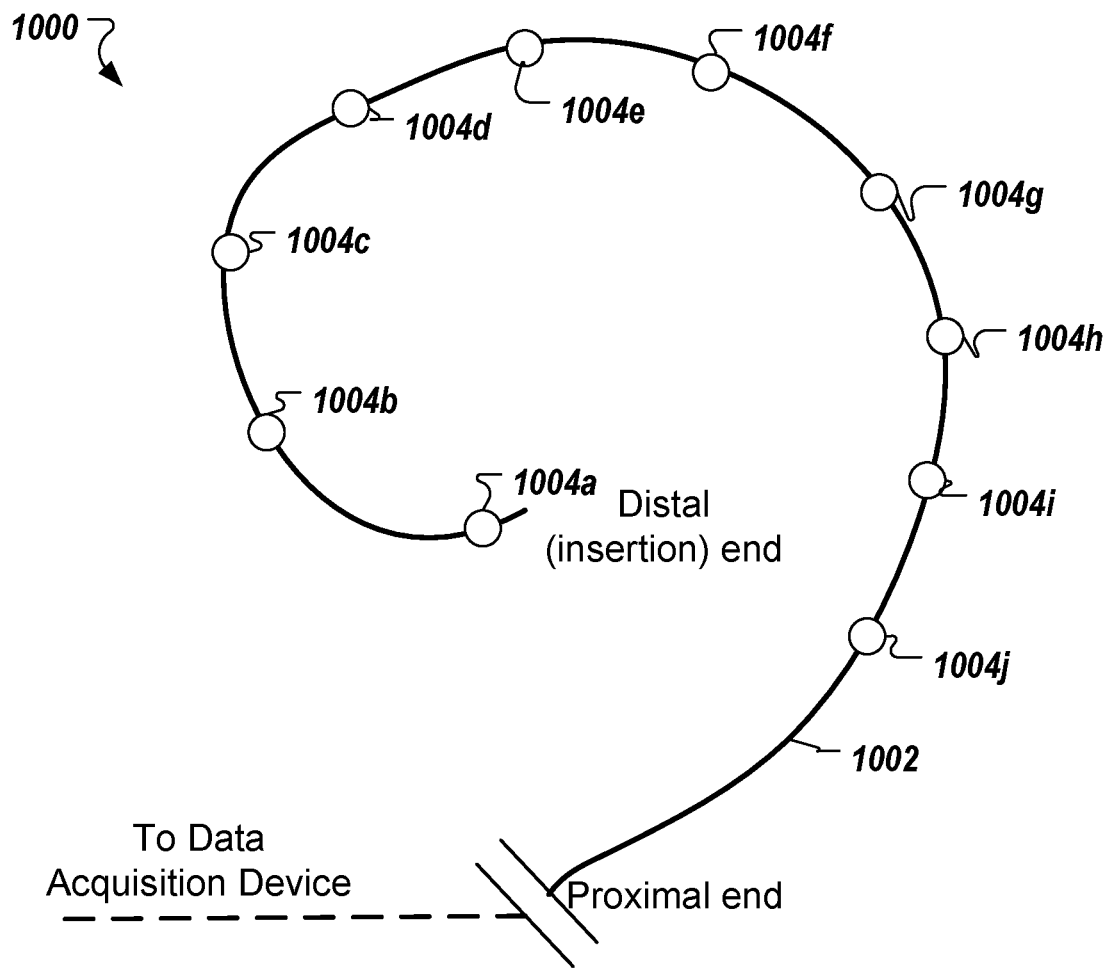
FIG. 10 shows an example curled multi-electrode device that is adapted for subcutaneous placement in a patient.

FIG. 10 depicts an example multi-electrode device 1000 that is adapted for subcutaneous placement in a patient. In some implementations, the device 1000 can be deployed to sense physiological electrical activity of a patient and to generate electrical ECG signals based on the sensed electrical activity. The ECG signals from the multi-electrode device 1000 may be processed, e.g., to assess a concentration of an analyte in a patient's bloodstream according to the techniques disclosed herein.

In general, the device 1000 includes an elongated spline 1002 and a set of electrodes 1004a-j spaced along the length of the spline 1002 (e.g., a multi-polar electrode device). The electrodes 1004a-j may be evenly or unevenly spaced along the length of the spline 1002. The spline 1002 may be curled or otherwise shaped, so as to create different vectors among each of the available pairs of electrodes 1004a-j. The different vectors result from the different positions of the electrodes 1004a-j with respect to each other, as each pair of electrodes is uniquely located and oriented when the device 1000 is deployed in a patient. In some implementations, the spline 1002 is formed from a metallic material (e.g., an aluminum alloy) that has memory to retain a given shape, but that can also be flexed, e.g., as may occur when the device 1000 is inserted into a patient. In some implementations, a distal end of the device 1000 is inserted straight into a patient's tissue subcutaneously. Due to the flexible, shape-retaining qualities of the spline 1002, the device 1000 curls as it is inserted into the patient to facilitate the multi-vector arrangement of electrodes 1004a-j. The spline 1002 itself, or additional wires along the spline 1002, may carry ECG signals to a data acquisition device that amplifies, filters, and digitizes the signals into computer-readable ECG data. In some implementations, the device 1000 may include a wireless RF transmitter that allows for wireless transmission of recorded ECG signals to an external computer. In other embodiments, the electrodes and splines are directly connected to implanted electronics that process and transmit the signal.

Figure 11:
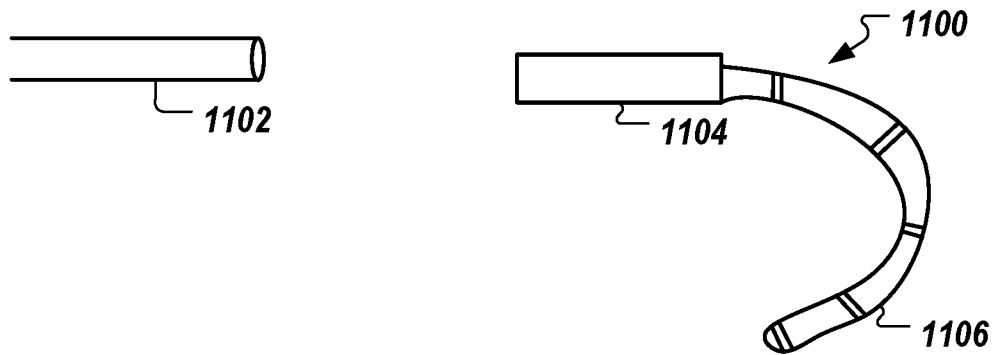
FIGS. 11-13 show various configurations of ECG electrodes that may be affixed to or otherwise used by a patient to sense signals for ECG data for different ECG vectors.
Figure 12:
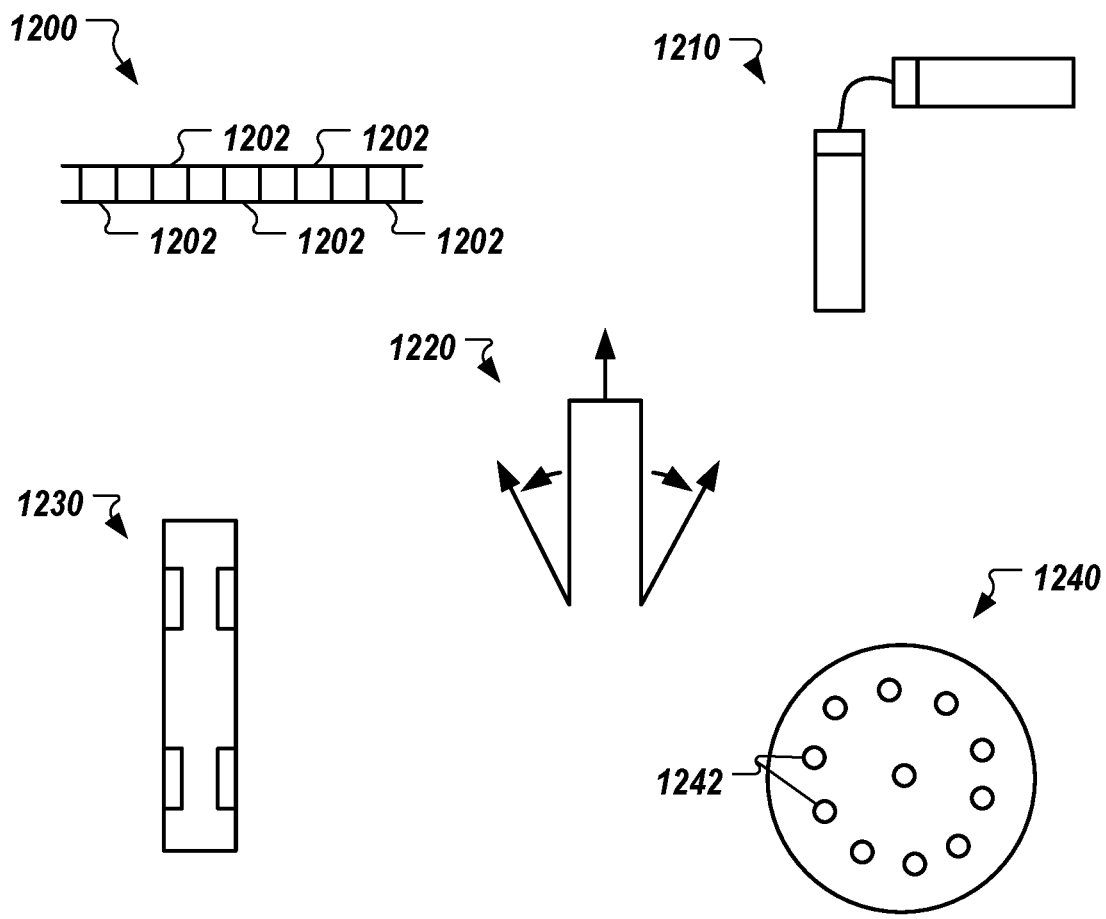
Figure 13:
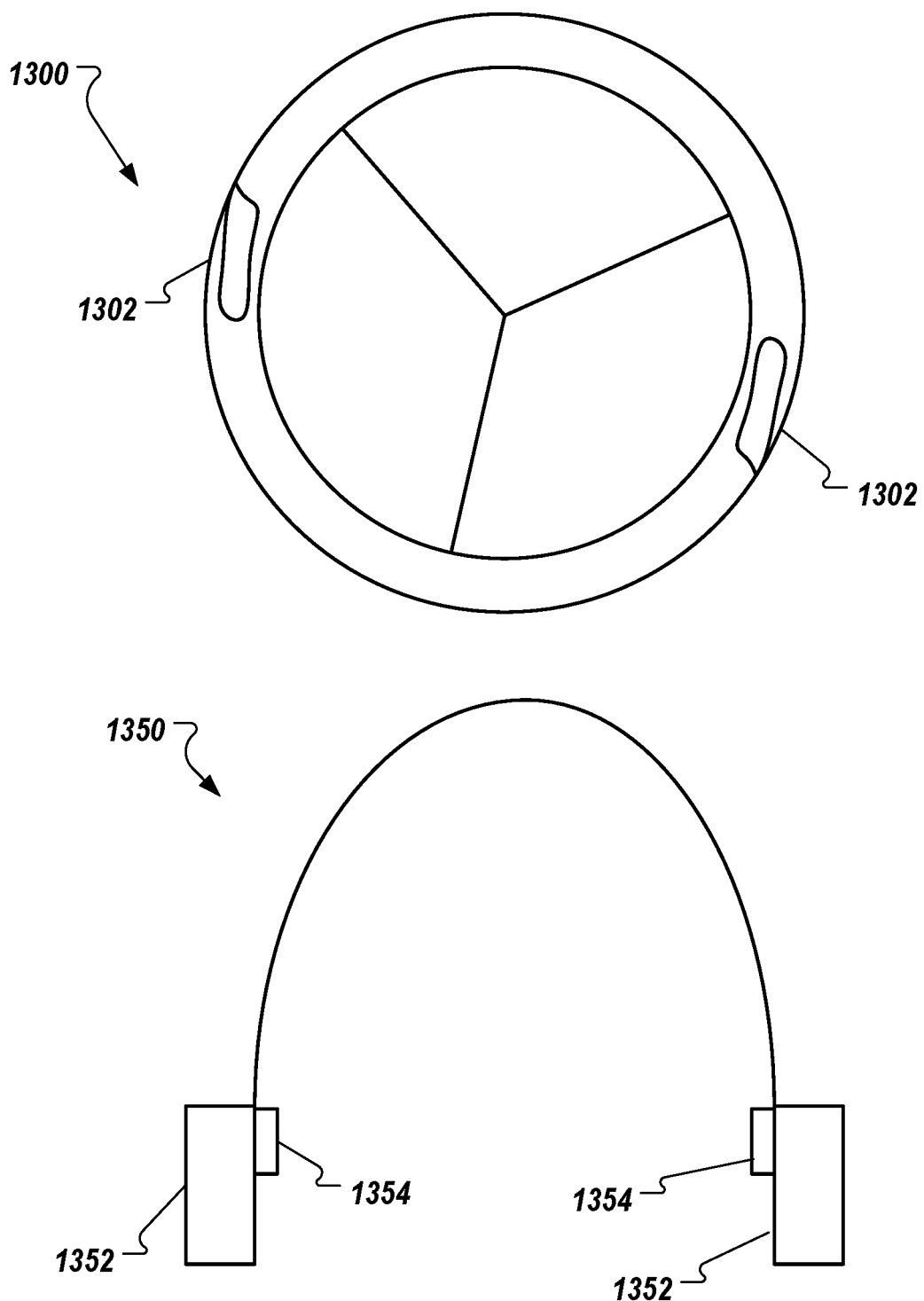

FIGS. 11-13 each show various configurations of ECG electrodes that may be affixed to a patient to sense signals for ECG data for different ECG vectors. Generally, electrodes may be incorporated into various goods that a patient may commonly interact with on a daily basis to facilitate ECG data acquisition and analyte assessments during common daily activities. For example, as shown in FIGS. 11-13, two or more electrodes may be incorporated into garments worn by a patient (e.g., a bra or sports shirt), a toilet seat, or a steering wheel. FIG. 11 shows an injector device 1102 and a flexible ECG electrode device 1100 that can be inserted subcutaneously. The electrode device 1100 has a body 1104 and flexible tail 1106 with bands of electrodes. FIG. 12 shows various additional electrode devices 1200, 1210, 1220, 1230, and 1240. For example a circular patch 1240 having a set of electrodes 1242 can be provided for subcutaneous applications. In some implementations, the patch 1240 further includes one or more accelerometers, gyroscopes, and/or other orientation and motion sensors to measure the patient's posture and movements. FIG. 13 shows a steering wheel 1300 having ECG electrodes 1302 along the perimeter of the wheel so that an ECG can be detected from the driver's hands while driving. Additionally, headphones 1350 have ECG electrodes 1354 located at the head-facing sides of the speaker assemblies 1352 (additionally/alternatively located in the band that extends over the wearer's head and connects the left and right speaker assemblies).

Figure 14:
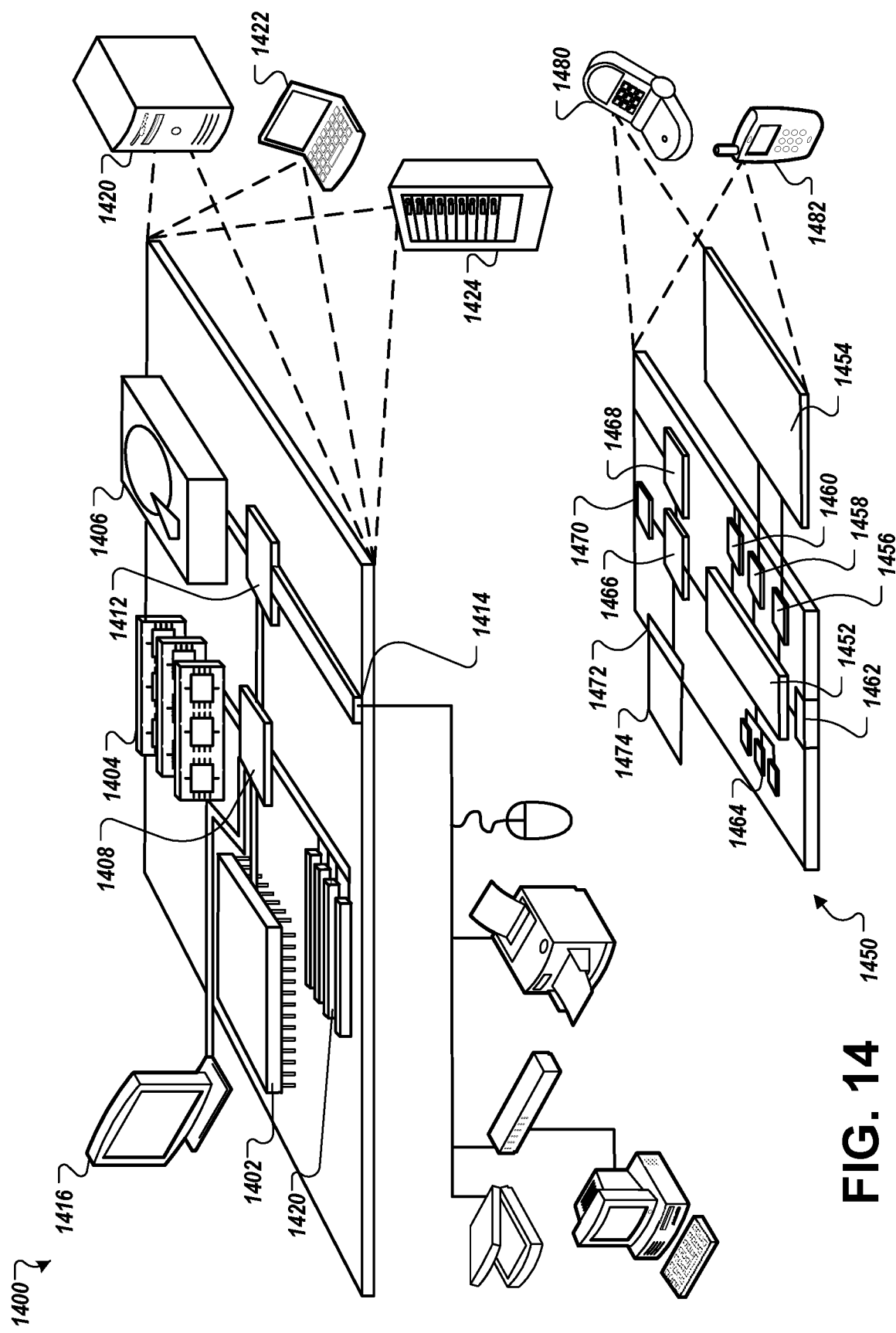
FIG. 14 is a block diagram of example computing devices that may be used to implement the systems, methods, devices, and other described in this specification, as either a client or as a server or plurality of servers.

FIG. 14 is a block diagram of computing devices 1400, 1450 that may be used to implement the systems and methods described in this document, as either a client or as a server or plurality of servers. Computing device 1400 is intended to represent various forms of digital computers, such as laptops, desktops, workstations, personal digital assistants, servers, blade servers, mainframes, and other appropriate computers. Computing device 1450 is intended to represent various forms of mobile devices, such as personal digital assistants, cellular telephones, smartphones, and other similar computing devices. Additionally computing device 1400 or 1450 can include Universal Serial Bus (USB) flash drives. The USB flash drives may store operating systems and other applications. The USB flash drives can include input/output components, such as a wireless transmitter or USB connector that may be inserted into a USB port of another computing device. The components shown here, their connections and relationships, and their functions, are meant to be exemplary only, and are not meant to limit implementations described and/or claimed in this document.

Computing device 1400 includes a processor 1402, memory 1404, a storage device 1406, a high-speed interface 1408 connecting to memory 1404 and high-speed expansion ports 1410, and a low speed interface 1412 connecting to low speed bus 1414 and storage device 1406. Each of the components 1402, 1404, 1406, 1408, 1410, and 1412, are interconnected using various busses, and may be mounted on a common motherboard or in other manners as appropriate. The processor 1402 can process instructions for execution within the computing device 1400, including instructions stored in the memory 1404 or on the storage device 1406 to display graphical information for a GUI on an external input/output device, such as display 1416 coupled to high speed interface 1408. In other implementations, multiple processors and/or multiple buses may be used, as appropriate, along with multiple memories and types of memory. Also, multiple computing devices 1400 may be connected, with each device providing portions of the necessary operations (e.g., as a server bank, a group of blade servers, or a multi-processor system).

The memory 1404 stores information within the computing device 1400. In one implementation, the memory 1404 is a volatile memory unit or units. In another implementation, the memory 1404 is a non-volatile memory unit or units. The memory 1404 may also be another form of computer-readable medium, such as a magnetic or optical disk.

The storage device 1406 is capable of providing mass storage for the computing device 1400. In one implementation, the storage device 1406 may be or contain a computer-readable medium, such as a floppy disk device, a hard disk device, an optical disk device, or a tape device, a flash memory or other similar solid state memory device, or an array of devices, including devices in a storage area network or other configurations. A computer program product can be tangibly embodied in an information carrier. The computer program product may also contain instructions that, when executed, perform one or more methods, such as those described above. The information carrier is a computer- or machine-readable medium, such as the memory 1404, the storage device 1406, or memory on processor 1402.

The high speed controller 1408 manages bandwidth-intensive operations for the computing device 1400, while the low speed controller 1412 manages lower bandwidth-intensive operations. Such allocation of functions is exemplary only. In one implementation, the high-speed controller 1408 is coupled to memory 1404, display 1416 (e.g., through a graphics processor or accelerator), and to high-speed expansion ports 1410, which may accept various expansion cards (not shown). In the implementation, low-speed controller 1412 is coupled to storage device 1406 and low-speed expansion port 1414. The low-speed expansion port, which may include various communication ports (e.g., USB, Bluetooth, Ethernet, wireless Ethernet) may be coupled to one or more input/output devices, such as a keyboard, a pointing device, a scanner, or a networking device such as a switch or router, e.g., through a network adapter.

The computing device 1400 may be implemented in a number of different forms, as shown in the figure. For example, it may be implemented as a standard server 1420, or multiple times in a group of such servers. It may also be implemented as part of a rack server system 1424. In addition, it may be implemented in a personal computer such as a laptop computer 1422. Alternatively, components from computing device 1400 may be combined with other components in a mobile device (not shown), such as device 1450. Each of such devices may contain one or more of computing device 1400, 1450, and an entire system may be made up of multiple computing devices 1400, 1450 communicating with each other.

Computing device 1450 includes a processor 1452, memory 1464, an input/output device such as a display 1454, a communication interface 1466, and a transceiver 1468, among other components. The device 1450 may also be provided with a storage device, such as a microdrive or other device, to provide additional storage. Each of the components 1450, 1452, 1464, 1454, 1466, and 1468, are interconnected using various buses, and several of the components may be mounted on a common motherboard or in other manners as appropriate.

The processor 1452 can execute instructions within the computing device 1450, including instructions stored in the memory 1464. The processor may be implemented as a chipset of chips that include separate and multiple analog and digital processors. Additionally, the processor may be implemented using any of a number of architectures. For example, the processor 1452 may be a CISC (Complex Instruction Set Computers) processor, a RISC (Reduced Instruction Set Computer) processor, or a MISC (Minimal Instruction Set Computer) processor. The processor may provide, for example, for coordination of the other components of the device 1450, such as control of user interfaces, applications run by device 1450, and wireless communication by device 1450.

Processor 1452 may communicate with a user through control interface 1458 and display interface 1456 coupled to a display 1454. The display 1454 may be, for example, a TFT (Thin-Film-Transistor Liquid Crystal Display) display or an OLED (Organic Light Emitting Diode) display, or other appropriate display technology. The display interface 1456 may comprise appropriate circuitry for driving the display 1454 to present graphical and other information to a user. The control interface 1458 may receive commands from a user and convert them for submission to the processor 1452. In addition, an external interface 1462 may be provide in communication with processor 1452, so as to enable near area communication of device 1450 with other devices. External interface 1462 may provide, for example, for wired communication in some implementations, or for wireless communication in other implementations, and multiple interfaces may also be used.

The memory 1464 stores information within the computing device 1450. The memory 1464 can be implemented as one or more of a computer-readable medium or media, a volatile memory unit or units, or a non-volatile memory unit or units. Expansion memory 1474 may also be provided and connected to device 1450 through expansion interface 1472, which may include, for example, a SIMM (Single In Line Memory Module) card interface. Such expansion memory 1474 may provide extra storage space for device 1450, or may also store applications or other information for device 1450. Specifically, expansion memory 1474 may include instructions to carry out or supplement the processes described above, and may include secure information also. Thus, for example, expansion memory 1474 may be provide as a security module for device 1450, and may be programmed with instructions that permit secure use of device 1450. In addition, secure applications may be provided via the SIMM cards, along with additional information, such as placing identifying information on the SIMM card in a non-hackable manner.

The memory may include, for example, flash memory and/or NVRAM memory, as discussed below. In one implementation, a computer program product is tangibly embodied in an information carrier. The computer program product contains instructions that, when executed, perform one or more methods, such as those described above. The information carrier is a computer- or machine-readable medium, such as the memory 1464, expansion memory 1474, or memory on processor 1452 that may be received, for example, over transceiver 1468 or external interface 1462.

Device 1450 may communicate wirelessly through communication interface 1466, which may include digital signal processing circuitry where necessary. Communication interface 1466 may provide for communications under various modes or protocols, such as GSM voice calls, SMS, EMS, or MMS messaging, CDMA, TDMA, PDC, WCDMA, CDMA2000, or CPRS, among others. Such communication may occur, for example, through radio-frequency transceiver 1468. In addition, short-range communication may occur, such as using a Bluetooth, WiFi, or other such transceiver (not shown). In addition, GPS (Global Positioning System) receiver module 1470 may provide additional navigation- and location-related wireless data to device 1450, which may be used as appropriate by applications running on device 1450.

Device 1450 may also communicate audibly using audio codec 1460, which may receive spoken information from a user and convert it to usable digital information. Audio codec 1460 may likewise generate audible sound for a user, such as through a speaker, e.g., in a handset of device 1450. Such sound may include sound from voice telephone calls, may include recorded sound (e.g., voice messages, music files, etc.) and may also include sound generated by applications operating on device 1450.

The computing device 1450 may be implemented in a number of different forms, as shown in the figure. For example, it may be implemented as a cellular telephone 1480. It may also be implemented as part of a smartphone 1482, personal digital assistant, or other similar mobile device.

Various implementations of the systems and techniques described here can be realized in digital electronic circuitry, integrated circuitry, specially designed ASICs (application specific integrated circuits), computer hardware, firmware, software, and/or combinations thereof. These various implementations can include implementation in one or more computer programs that are executable and/or interpretable on a programmable system including at least one programmable processor, which may be special or general purpose, coupled to receive data and instructions from, and to transmit data and instructions to, a storage system, at least one input device, and at least one output device.

These computer programs (also known as programs, software, software applications or code) include machine instructions for a programmable processor, and can be implemented in a high-level procedural and/or object-oriented programming language, and/or in assembly/machine language. As used herein, the terms "machine-readable medium" "computer-readable medium" refers to any computer program product, apparatus and/or device (e.g., magnetic discs, optical disks, memory, Programmable Logic Devices (PLDs)) used to provide machine instructions and/or data to a programmable processor, including a machine-readable medium that receives machine instructions as a machine-readable signal. The term "machine-readable signal" refers to any signal used to provide machine instructions and/or data to a programmable processor.

To provide for interaction with a user, the systems and techniques described here can be implemented on a computer having a display device (e.g., a CRT (cathode ray tube) or LCD (liquid crystal display) monitor) for displaying information to the user and a keyboard and a pointing device (e.g., a mouse or a trackball) by which the user can provide input to the computer. Other kinds of devices can be used to provide for interaction with a user as well; for example, feedback provided to the user can be any form of sensory feedback (e.g., visual feedback, auditory feedback, or tactile feedback); and input from the user can be received in any form, including acoustic, speech, or tactile input.

The systems and techniques described here can be implemented in a computing system that includes a back end component (e.g., as a data server), or that includes a middleware component (e.g., an application server), or that includes a front end component (e.g., a client computer having a graphical user interface or a Web browser through which a user can interact with an implementation of the systems and techniques described here), or any combination of such back end, middleware, or front end components. The components of the system can be interconnected by any form or medium of digital data communication (e.g., a communication network). Examples of communication networks include a local area network ("LAN"), a wide area network ("WAN"), peer-to-peer networks (having ad-hoc or static members), grid computing infrastructures, and the Internet.

The computing system can include clients and servers. A client and server are generally remote from each other and typically interact through a communication network. The relationship of client and server arises by virtue of computer programs running on the respective computers and having a client-server relationship to each other.

Although a few implementations have been described in detail above, other modifications are possible. Moreover, other mechanisms quantifying potassium based on ECG data may be used. In addition, the logic flows depicted in the figures do not require the particular order shown, or sequential order, to achieve desirable results. Other steps may be provided, or steps may be eliminated, from the described flows, and other components may be added to, or removed from, the described systems. Accordingly, other implementations are within the scope of the following claims.

What is claimed is:

1. A computer-implemented method, comprising:
receiving, by a computing system, electrocardiogram (ECG) data that specifies measurements from an ECG of a patient during a first time interval, wherein the measurements in the ECG data indicate levels of ECG signals for a plurality of leads sensed by electrodes physically coupled to the patient;
determining, by the computing system, a position of the patient during the first time interval;
analyzing, by the computing system, the ECG data to determine first values for a first set of waveform features for an ECG vector of a particular pair of leads of the plurality of leads in the ECG of the patient;

determining that the position of the patient during the first time interval does not match a pre-defined baseline position of the patient, and in response, selecting the particular pair of leads, from among the plurality of leads, from which to estimate a level of an analyte present in the patient during the first time interval, wherein the particular pair of leads is selected from among the plurality of leads based on a level of similarity between the first values for the first set of waveform features for the ECG vector for the particular pair of leads and pre-defined values for the first set of waveform features;

generating an estimation of the level of the analyte present in the patient during the first time interval based on an identified correlation between a level of the analyte and at least one of (i) second values for a second set of waveform features of the ECG vector for the particular pair of leads or (ii) third values for waveform features of a derived ECG vector computed using the ECG vector for the particular pair of leads, wherein the second set of waveform features includes at least one waveform feature that is not among the first set of waveform features; and providing an indication of the estimated level of the analyte that was present in the patient during the first time interval.

2. The computer-implemented method of claim 1, wherein:

the first values for the first set of waveform features represent values of features of a QRS-complex of the ECG vector for the particular pair of leads; and the pre-defined values for the first set of waveform features represent values of features of a QRS-complex of an ECG vector for a second pair of leads, among the plurality of leads, for ECG data that specifies measurements from an ECG of the patient during a previous time interval in which the position of the patient matched the pre-defined baseline position.

3. The computer-implemented method of claim 2, wherein the features of the QRS-complex of the ECG vector for the particular pair of leads comprise at least one of an area of the QRS-complex or a portion thereof, a slope of the QRS-complex or a portion thereof, a center-of-gravity of the QRS-complex or a portion thereof, or an amplitude of the QRS-complex or a portion thereof.

4. The computer-implemented method of claim 2, comprising determining a level of similarity between the values of the features of the QRS-complex of the ECG vector for the particular pair of leads and the values of the features of the QRS-complex of the ECG vector for the second pair of leads, including time warping the QRS-complex of the ECG vector for the particular pair of leads and determining a correlation between the time-warped QRS-complex of the ECG vector for the particular pair of leads and the QRS-complex of the ECG vector for the second pair of leads.

5. The computer-implemented method of claim 1, wherein the plurality of leads are provided on a single patch configured to adhere to a surface of the patient.

6. The computer-implemented method of claim 5, wherein the plurality of leads are arranged in a circular pattern on the single patch.

7. The computer-implemented method of claim 1, further comprising:

receiving, by the computing system, orientation-motion data that represents at least one of an orientation of the patient during the first time interval or a movement of the patient during the first time interval; and determining the position of the patient during the first time interval based on the orientation-motion data.

8. The computer-implemented method of claim 7, wherein the orientation-motion data is derived at least in part from a signal sensed by at least one of an accelerometer, a gyroscope, a gravity sensor, a magnetometer, a compass, or a rotational vector sensor.

9. The computer-implemented method of claim 1, wherein providing the indication of the estimated level of the analyte that was present in the patient during the first time interval comprises displaying or storing a representation of the estimated level of the analyte.

10. The computer-implemented method of claim 1, wherein generating the estimation of the level of the analyte present in the patient during the first time interval comprises:

determining values for a set of features that characterize a T-wave of the ECG vector for the particular pair of leads or of the derived ECG vector computed using the ECG vector for the particular pair of leads; and evaluating the values for the determined set of features that characterize the T-wave with respect to a model that correlates T-wave features with estimated levels of the analyte present in the patient.

11. The computer-implemented method of claim 1, wherein the analyte comprises at least one of potassium, magnesium, or phosphorous.

12. The computer-implemented method of claim 1, comprising selecting the particular pair of leads from which to estimate the level of the analyte present in the patient further in response to determining that a level of movement of the patient during the first time interval is less than a pre-specified maximum-acceptable level of movement.

13. The computer-implemented method of claim 1, comprising determining the pre-defined values for the first set of waveform features based on second ECG data that specifies measurements from an ECG of the patient during a second time interval in which the patient was in a position that matches the pre-defined baseline position.

14. The computer-implemented method of claim 1, further comprising:

receiving, by the computing system, second ECG data that specifies measurements from an ECG of the patient during a second time interval subsequent to the first time interval;

determining, by the computing system, that a position of the patient during the second time interval matches the pre-defined baseline position of the patient; and in response to determining that the position of the patient during the second time interval matches the pre-defined baseline position of the patient, updating the pre-defined values for the first set of waveform features using the second ECG data.

15. The computer-implemented method of claim 1, wherein selecting the particular pair of leads comprises:

for each of a plurality of lead pairs consisting of different leads from the plurality of leads, determining a respective ECG vector for the particular lead pair and values of respective waveform features of the respective ECG vector for the particular lead pair; and selecting the particular pair of leads from among the plurality of lead pairs as a result of values of waveform features of the ECG vector for the particular pair of leads most closely matching the pre-defined values for the first set of waveform features.

16. The computer-implemented method of claim 1, wherein the pre-defined values for the first set of waveform features are determined from ECG data specifies measurements from an ECG of the patient during a preceding time interval before the first time interval in which the patient was in the baseline position.

17. One or more non-transitory computer-readable media having instructions stored thereon that, when executed by one or more processors, cause performance of operations comprising:
  receiving, by a computing system, electrocardiogram (ECG) data that specifies measurements from an ECG of a patient during a first time interval, wherein the measurements in the ECG data indicate levels of ECG signals for a plurality of leads sensed by electrodes physically coupled to the patient;
  determining, by the computing system, a position of the patient during the first time interval;
  analyzing, by the computing system, the ECG data to determine first values for a first set of waveform features for an ECG vector of a particular pair of leads of the plurality of leads in the ECG of the patient;
  determining that the position of the patient during the first time interval does not match a pre-defined baseline position of the patient, and in response, selecting the particular pair of leads, from among the plurality of leads, from which to estimate a level of an analyte present in the patient during the first time interval, wherein the particular pair of leads is selected from among the plurality of leads based on a level of similarity between the first values for the first set of waveform features for the ECG vector for the particular pair of leads and pre-defined values for the first set of waveform features;
  generating an estimation of the level of the analyte present in the patient during the first time interval based on an identified correlation between a level of the analyte and at least one of (i) second values for a second set of waveform features of the ECG vector for the particular pair of leads or (ii) third values for waveform features of a derived ECG vector computed using the ECG vector for the particular pair of leads, wherein the second set of waveform features includes at least one waveform feature that is not among the first set of waveform features; and
  providing an indication of the estimated level of the analyte that was present in the patient during the first time interval.

18. The one or more non-transitory computer-readable media of claim 17, wherein the plurality of leads are provided on a single patch configured to adhere to a surface of the patient.

19. The one or more non-transitory computer-readable media of claim 18, wherein the plurality of leads are arranged in a circular pattern on the single patch.

20. The one or more non-transitory computer-readable media of claim 17, wherein the operations further comprise:
  receiving, by the computing system, orientation-motion data that represents at least one of an orientation of the patient during the first time interval or a movement of the patient during the first time interval; and
  determining the position of the patient during the first time interval based on the orientation-motion data.

21. The one or more non-transitory computer-readable media of claim 17, wherein the pre-defined values for the first set of waveform features are determined from ECG data specifies measurements from an ECG of the patient during a preceding time interval before the first time interval in which the patient was in the baseline position.

22. A computing system comprising:
  one or more processors; and
  one or more non-transitory computer-readable media having instructions stored thereon that, when executed by the one or more processors, cause performance of operations comprising:
    receiving, by the computing system, electrocardiogram (ECG) data that specifies measurements from an ECG of a patient during a first time interval, wherein the measurements in the ECG data indicate levels of ECG signals for a plurality of leads sensed by electrodes physically coupled to the patient;
    determining, by the computing system, a position of the patient during the first time interval;
    analyzing, by the computing system, the ECG data to determine first values for a first set of waveform features for an ECG vector of a particular pair of leads of the plurality of leads in the ECG of the patient;
    determining that the position of the patient during the first time interval does not match a pre-defined baseline position of the patient, and in response, selecting the particular pair of leads, from among the plurality of leads, from which to estimate a level of an analyte present in the patient during the first time interval, wherein the particular pair of leads is selected from among the plurality of leads based on a level of similarity between the first values for the first set of waveform features for the ECG vector for the particular pair of leads and pre-defined values for the first set of waveform features;
    generating an estimation of the level of the analyte present in the patient during the first time interval based on an identified correlation between a level of the analyte and at least one of (i) second values for a second set of waveform features of the ECG vector for the particular pair of leads or (ii) third values for waveform features of a derived ECG vector computed using the ECG vector for the particular pair of leads, wherein the second set of waveform features includes at least one waveform feature that is not among the first set of waveform features; and
    providing an indication of the estimated level of the analyte that was present in the patient during the first time interval.

23. The computing system of claim 22, wherein the pre-defined values for the first set of waveform features are determined from ECG data specifies measurements from an ECG of the patient during a preceding time interval before the first time interval in which the patient was in the baseline position.

* * * * *